United States Patent [19]
Toran-Allerand

[11] Patent Number: 5,990,078
[45] Date of Patent: Nov. 23, 1999

[54] MEANS OF INCREASING ESTROGEN RECEPTOR LEVELS IN NEURAL TISSUE

[75] Inventor: C. Dominique Toran-Allerand, New York, N.Y.

[73] Assignee: The Trustees of Columbia University in the City of New York, New York, N.Y.

[21] Appl. No.: 08/679,628

[22] Filed: Jul. 12, 1996

Related U.S. Application Data

[60] Provisional application No. 60/001,195, Jul. 14, 1995.

[51] Int. Cl.$^6$ .......................... A61K 38/18; A61K 31/56; C07K 14/475
[52] U.S. Cl. ............................... 514/2; 514/12; 514/182; 530/399; 540/2; 540/114; 540/117
[58] Field of Search .................................. 514/8, 12, 21; 530/399, 514, 540, 182, 2, 114, 117

[56] References Cited

PUBLICATIONS

Toran–Allerand et. al, PNAS, vol. 89, May 1992, pp. 4668–4672.

Miranda et al, PNAS, vol. 90, Jul. 1993, pp. 6439–6443.

McMillan, P.J., et al. (1996) The Effects of Ovariectomy and Estrogen Replacement on trkA and Choline Acetyltransferase mRNA Expression in the Basal Forebrain of the Adult Female Sprague–Dawley Rat. *J. Neurosci.* 16(5):1860–1865. (Exhibit B).

Miranda, R.C., et al. (1994) Interactions of Estrogen with the Neurotrophins and Their Receptors During Neural Development *Hormones and Behavior* 28:367–375. (Exhibit C).

Miranda, R.C., et al. (1993) Neuronal Colocalization of mRNAs for Neurotrophins and Their Receptors in the Developing Central Nervous System Suggests a Potential for Autocrine Interactions *Proc. Natl. Acad. Sci. USA* 90:6439–6443. (Exhibit D).

Miranda, R.C., et al. (1993) Presumptive Estrogen Target Neurons Express mRNAs for both the Neurotrophins and Neurotrophin Receptors: A Basis for Potential Developmental Interactions of Estrogen with the Neurotrophins *Molecular and Cellular Neurosciences* 4(6):510–525 (Exhibit E).

Miranda, R.C., and Toran–Allerand, C.D. (1992) Developmental Expression of Estrogen Receptor mRNA in the Rat Cerebral Cortex: A Nonisotopic in situ Hybridization Histochemistry Study *Cerebral Cortex* 2:1–15. (Exhibit F).

Singh, M., et al. (1995) The Effect of Ovariectomy and Estradiol Replacement on Brain–Derived Neurotrophic Factor Messenger Ribonucleic Acid Expression in Cortical and Hippocampal Brain Regions of Female Sprague–Dawley Rats *Endocrinology* 136(5):2320–2324 (Exhibit G).

Singh, M., et al (1993) Ovariectomy Reduces ChAT Activity and NGF mRNA Levels in the Frontal Cortex and Hippocampus of the Female Sprague–Dawley Rat *Society for Neuroscience Abstracts* 19(2):1254, Abstract No. 514.11. (Exhibit H).

Shorabji, F., et al (1995) Identification of a Putative Estrogen Response Element in the Gene Encoding Brain–Derived Neurotrophic Factor *Proc. Natl. Acad. Sci. USA* 92:11110–11114. (Exhibit I).

Sohrabji, F., et al. (1994) Reciprocal Regulation of Estrogen and NGF Receptors by Their Ligands in PC12 Cells *J. Neurobiology* 25(8):974–988. (Exhibit J).

Sohrabji, F. et al. (1994) Estrogen Differentially Regulates Estrogen and Nerve Growth Factor Receptor mRNAs in Adult Sensory Neurons *J. Neurosci.* 14(2):459–471. (Exhibit K).

Toran–Allerand, C.D. (1996) The Estrogen/Neurotrophin Connection During Neural Development: Is Co–Localization of Estrogen Receptors with the Neurotrophins and Their Receptors Biologically Relevant? *Dev. Neurosci.* 18:36–48. (Exhibit L).

Toran–Allerand, C.D. (1996) Mechanisms of Estrogen Action During Neural Development: Mediation by Interactions with the Neurotrophins and Their Receptors? *J. Steroid Biochem. Molec. Biol.* 56:169–178. (Exhibit M).

Toran–Allerand, C.D., et al. (1992) Estrogen Receptors Colocalize with Low–Affinity Nerve Growth Factor Receptors in Cholinergic Neurons of the Basal Forebrain *Proc. Natl. Acad. Sci. USA* 89:4668–4672. (Exhibit N).

Toran–Allerand, C.D., et al. (1992) Cellular Variations in Estrogen Receptor mRNA Translation in the Developing Brain: Evidence from Combined [$^{125}$I] Estrogen Autoradiography and Non–Isotopic In Situ Hybridization Histochemistry *Brain Research* 576:25–41. (Exhibit O).

Toran–Allerand, C.D. (1990) The Brain–Slicer: Anatomical Precision for Organotypic Explant Culture *Brain Research Bulletin* 24:865–868. (Exhibit P).

Toran–Allerand, C.D. (1984) in *Progress in Brain Research* G.J. DeVries et al. (Eds) On the Genesis of Sexual Differentiation of the Central Nervous System: Morphogenetic Consequences of Steroidal Exposure and Possible Role of α–Fetoprotein 61:63–98. (Exhibit Q).

(List continued on next page.)

*Primary Examiner*—Cecilia J. Tsang
*Assistant Examiner*—Anish Gupta
*Attorney, Agent, or Firm*—John P. White; Cooper & Dunham LLP

[57] ABSTRACT

This invention provides a method of increasing the level of estrogen receptors in the neural tissue of a subject which comprises administering to the subject estrogen in an amount effective to increase the level of neurotrophin receptors and a neurotrophin in an amount effective to increase the level of estrogen receptors, so as to thereby increase the level of estrogen receptors. This invention also provides a method of increasing the level of estrogen receptors in a sample of neural tissue from a subject which comprises contacting the sample with estrogen in an amount effective to increase the level of neurotrophin receptors and neurotrophin in an amount effective to increase the level of estrogen receptors, so as to thereby increase the level of estrogen receptors. Lastly, this invention provides a method of preventing the onset of Alzheimer's disease.

13 Claims, 13 Drawing Sheets

PUBLICATIONS

Toran–Allerand, C.D. (1976) Sex Steroids and the Development of the Newborn Mouse Hypothalamus and Preoptic Area In Vitro: Implications for Sexual Differentiation *Brain Research* 106:407–412. (Exhibit R).

Scisearch abstract on STN. No. 94:451363. Sohrabhi et al. 'Reciprocal Regulation of Estrogen and NGF Receptors by Their Ligands in PC12 Cells', Journal of Neurobiology, vol. 25, No. 8, pp. 974–988 (abstract), Jul. 1994.

Scisearch abstract on STN. No. 95:99583. Miranda et al. 'Interactions of Estrogen with the Neurotrophins and Their Receptors During Neural Development', Hormones and Behavior, vol. 28, No. 4, pp. 367–375 (abstract), Dec. 1994.

Ehlert et al., 'Muscarinic Receptors and Novel Strategies for the Treatment of Age–Related Brain Disorders', Life Sciences, vol. 55, Nos. 25/26, pp. 2135–2145, 1994.

Patel, Shirish V., 'Pharmacotheraphy of Cognitive Impairment in Alzheimer's Disease: A Review', J. Geriatr. Psychiatry. Neurol. vol. 8, pp. 81–95, Apr. 1995.

FIG. 1A
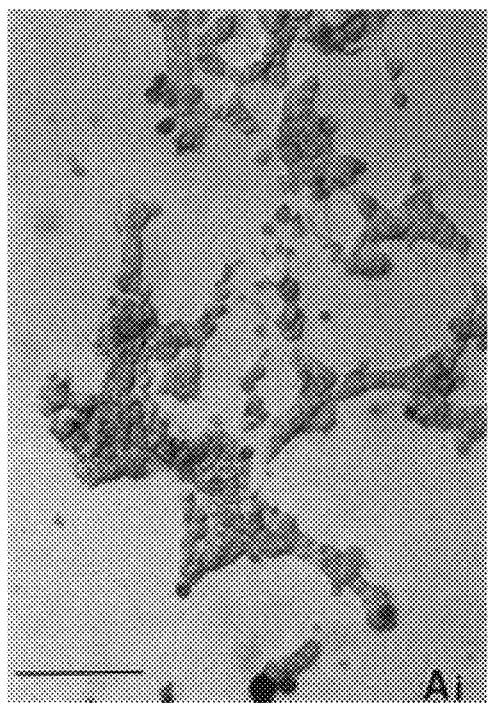
FIG. 1B
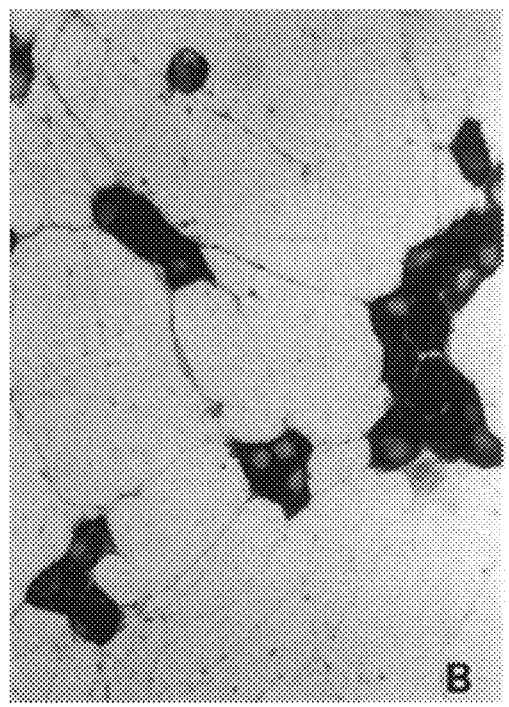
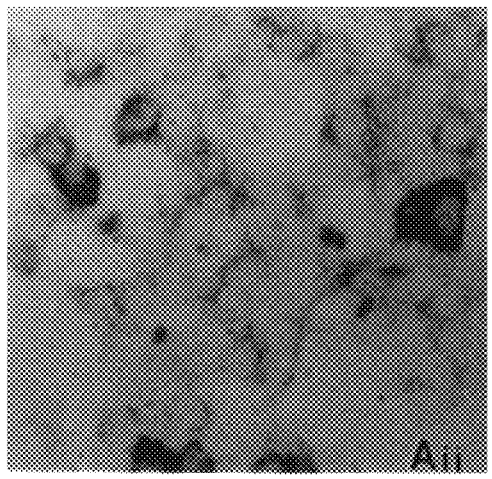
FIG. 1C

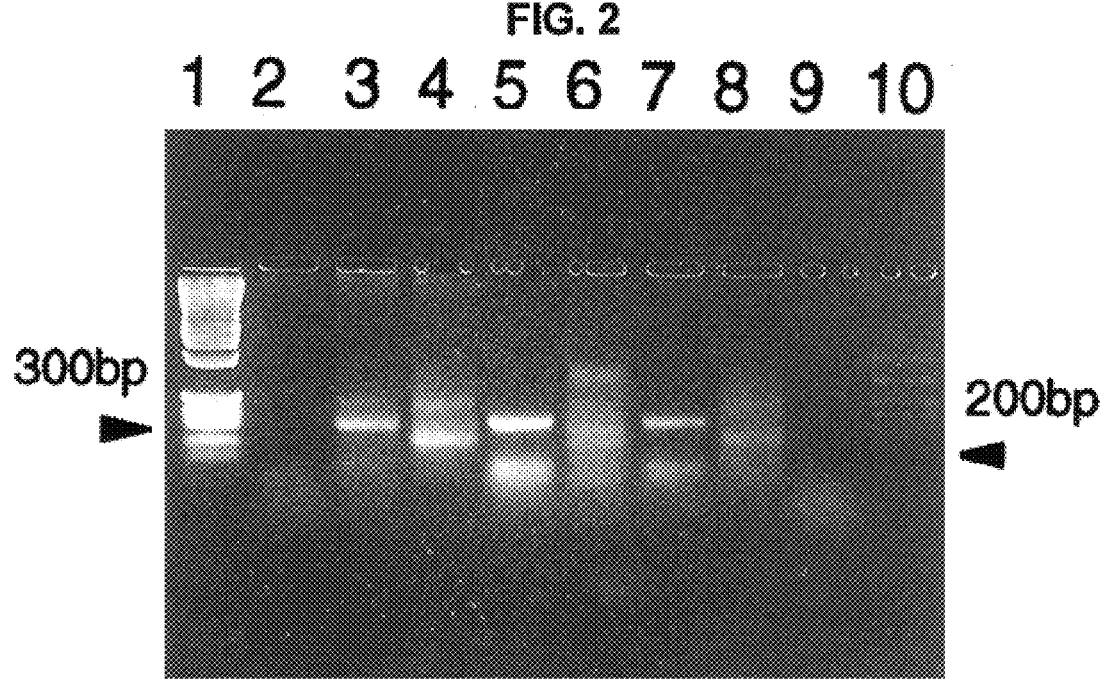

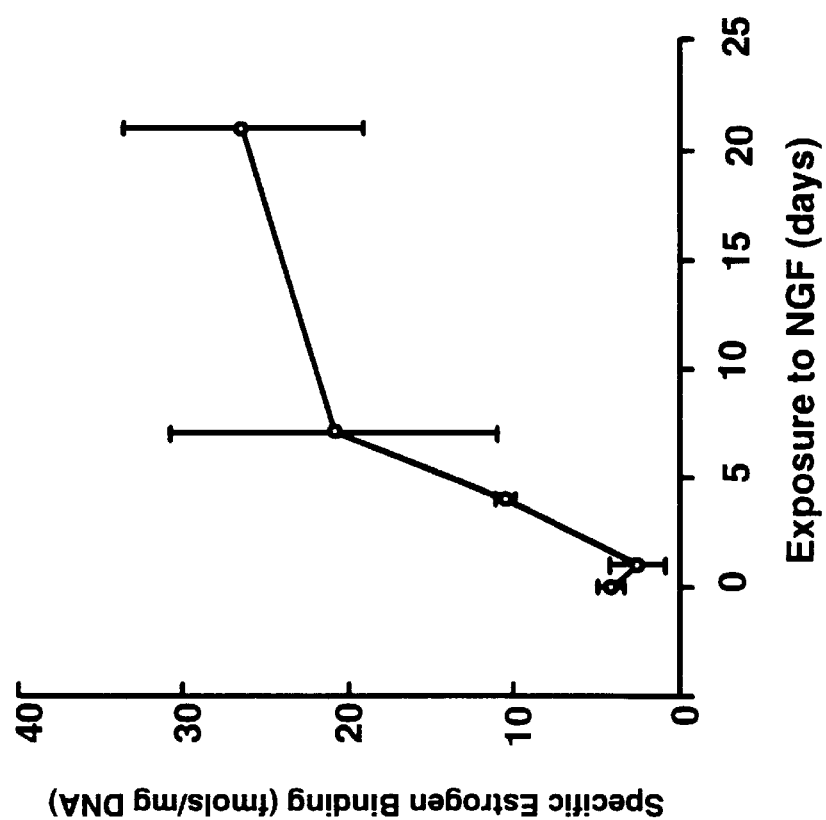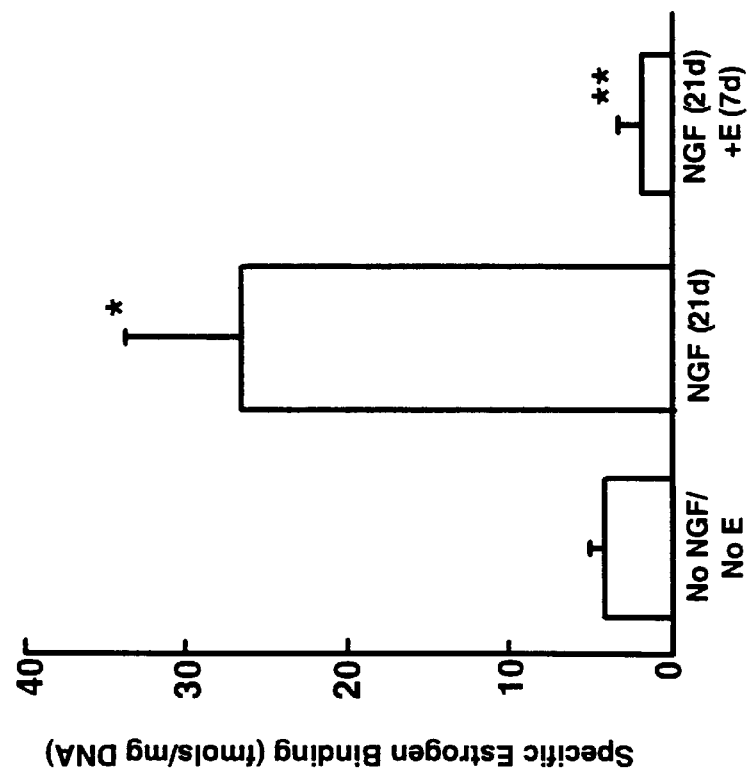
FIGURE 3A
FIGURE 3B

FIG. 5A
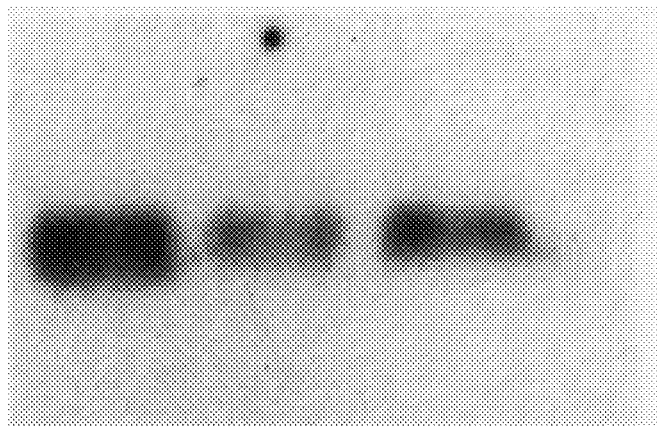
p75NGFR
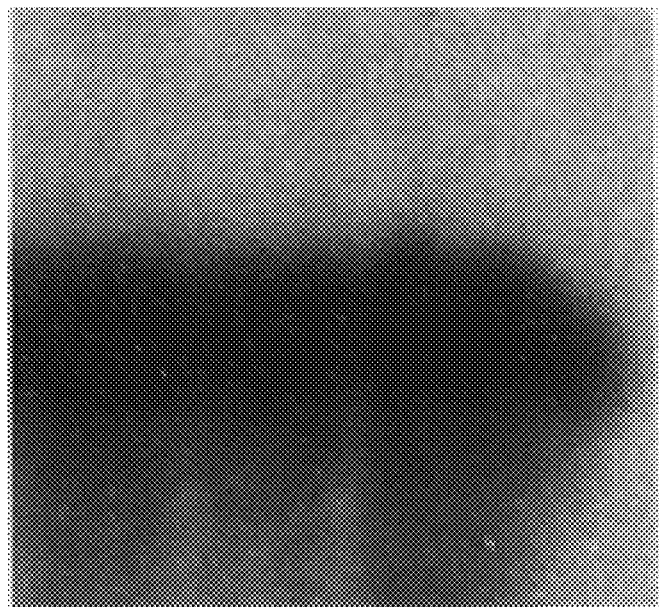
18S

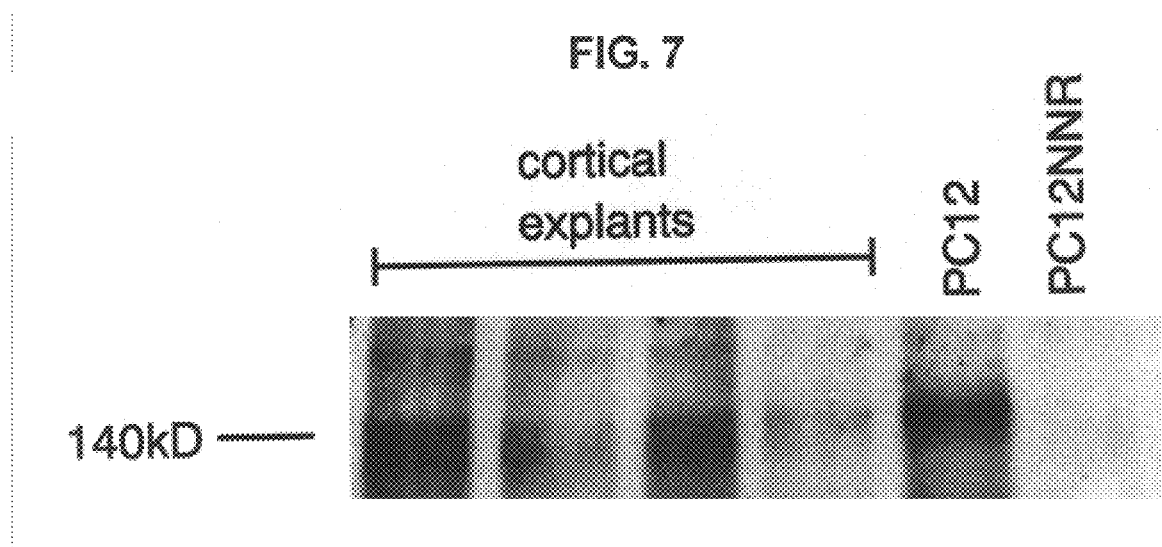

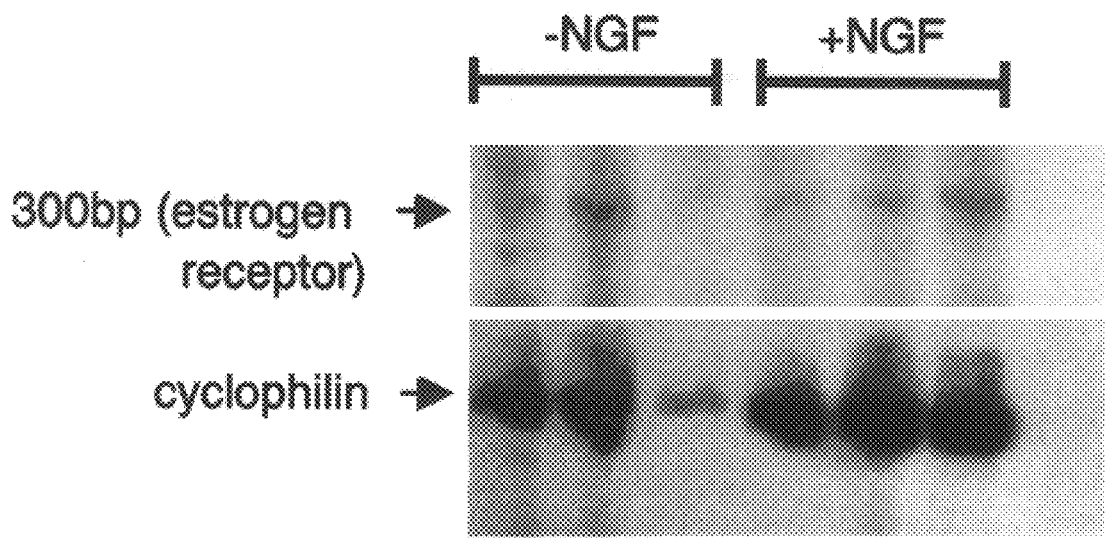

MEANS OF INCREASING ESTROGEN RECEPTOR LEVELS IN NEURAL TISSUE

This application claims benefit of U.S. provisional application Ser. No. 60/001,195, filed Jul. 14, 1995.

This invention was made with support under the following grants: Grant No. 08099 from the National Institutes of Health, U.S. Department of Health and Human Services; Grant No. 49682 from the National Institute of Mental Health; Grant No. 9109375 from the National Science Foundation; and Grant No. 00192 from the Alcohol, Drug and Mental Health Administration. Accordingly, the United States Government has certain rights in the invention.

Throughout this application, various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THE INVENTION

Both estrogen and the neurotrophins influence neural organization. The estrogen receptor, which mediates the biological response of the hormone, is expressed at high levels in the brain during development, and estrogen has been shown to promote growth in the developing nervous system, in vivo [39, 67, 77, 93, 94], in vitro [97-101] and in oculo [78]. Although estrogen receptor expression is more restricted in adulthood, estrogen continues to affect neuronal structure, physiology and gene expression in specific adult steroid targets [19, 21, 30, 68, 83].

Estrogen regulates transcription of a variety of structural proteins [38, 62, 94], steroid, peptide and neurotransmitter receptors [19, 21, 63], as well as hormones and neuropeptides [83, 110]. The estrogen receptor is a member of the superfamily of steroid/thyroid hormone/Vitamin $D_3$/retinoic acid receptors, capable of activating genes by directly binding DNA sites containing hormone-specific regulatory elements [4, 24, 79]. An estrogen response element (ERE) has been identified in several estrogen-responsive genes including vitellogenin [50], c-fos [109], prolactin [107] and b-luteinizing hormone [89], suggesting that, in some instances, steroid effects may be mediated through direct activation of relevant genes. Alternatively, as in extra-neural targets such as MCF-7 mammary tumor cells [20] and the uterus [73, 76], estrogen-inducible genes may be regulated secondarily, or consequent, to the action of estrogen on other endogenous transcription-regulating growth factors or their receptors [99, 102].

The currently identified members of the neurotrophin family of growth factors, nerve growth factor (NGF), brain-derived neurotrophic factor (BDNF) and neurotrophins-3 (NT-3) and -4/5 (NT-4/5), share marked similarities in their conserved sequences and structural domains and all bind to the pan-neurotrophin receptor, $p75^{NGFR}$, although they differ in their spatial and temporal patterns of neural expression and function [2, 12, 47, 65, 81]. Ligand specificity and signal transduction requires the neurotrophins to associate with appropriate members of the trk proto-oncogene receptor tyrosine kinase family (trkA, trkB, trkC) of membrane bound receptors [48, 53, 91, 92].

Both NGF and estrogen have been shown: 1) to promote survival and specific patterns of differentiation in their neuronal targets [55, 103], 2) to regulate the expression of primary (early) response genes such as c-fos and c-jun [17, 57, 108, 109, 111], 3) to regulate the activity of cholinergic enzymes in the developing [1, 4, 61] and adult basal forebrain [32, 43, 59, 60]. It has been shown that in neurons of the developing forebrain [72, 105, 106], estrogen receptors colocalize with $p75^{NGFR}$ mRNA and protein as well as mRNA for trkA (whose encoded protein binds NGF) [15, 48, 75] and trkB (whose encoded protein binds BDNF and NT-4/5) [45, 91, 92], indicating a biological substrate for possible interactions between estrogen and the neurotrophins. Analysis of the identified promoter region [88] of the $p75^{NGFR}$ [90, 105, 106] and 5'-region flanking the breakpoint of the trkA gene [90] indicates the presence of sequences with a high degree of homology to the putative vitellogenin and c-fos EREs, which is further consistent with the hypothesis that, in some instances, estrogen may regulate responsiveness to neurotrophins.

Co-localization of estrogen and neurotrophin receptor mRNA and protein [72, 105, 106] suggested that estrogen sensitivity may be a more general feature of neurotrophin targets. This hypothesis was tested in a previous study investigating the presence of estrogen receptor systems in a prototypic peripheral target of NGF, the dorsal root ganglion (DRG) of the adult female rat [90]. DRG neurons are dependent on NGF for their survival during development [2, 23, 46, 96] and in adulthood, following injury [16, 56, 82]. Both estrogen receptor mRNA and estrogen binding were found to be present in adult DRG neurons in vivo [90]. Moreover, in these neurons estrogen resulted in a two to three-fold increase in trkA mRNA and a transient decrease in $p75^{NGFR}$ mRNA.

SUMMARY OF THE INVENTION

This invention provides a method of increasing the level of estrogen receptors in a sample of neural tissue from a subject which comprises contacting the sample with: (a) estrogen in an amount effective to increase the level of neurotrophin receptors and (b) a neurotrophin in an amount effective to increase the level of estrogen receptors, so as to thereby increase the level of estrogen receptors in the neural tissue.

This invention provides a method of triggering gene regulation in a sample of neural tissue of a subject which comprises contacting the sample with (a) estrogen and (b) neurotrophin in effective amounts to induce tyrosine phosphorylation of the estrogen receptors and tyrosine phosphorylation of the neurotrophin receptors so as to trigger gene regulation.

This invention provides a method of increasing the level of estrogen receptors in neural tissue of a subject which comprises administering to the subject: (a) estrogen in an amount effective to increase the level of neurotrophin receptors and (b) a neurotrophin in an amount effective to increase the level of estrogen receptors, so as to thereby increase the level of estrogen receptors.

This invention provides a method of increasing the level of estrogen receptors in neural tissue of a subject which comprises administering to the subject: (a) estrogen in an amount effective to increase the level of neurotrophin receptors and (b) a neurotrophin conjugated to an antibody in an amount effective to increase the level of estrogen receptors, so as to thereby increase the level of estrogen receptors.

This invention provides a method of preventing the onset of Alzheimer's disease in a subject which comprises administering to the subject: (a) estrogen in an amount effective to increase the level of neurotrophin receptors and (b) a neurotrophin in an amount effective to increase the level of estrogen receptors, so as to thereby prevent the onset of Alzheimer's disease in the subject.

This invention provides a method of preventing the onset of Alzheimer's disease in a subject which comprises administering to the subject: (a) estrogen in an amount effective to increase the level of neurotrophin receptors and (b) a neurotrophin conjugated to an antibody in an amount effective to increase the level of estrogen receptors, so as to thereby prevent the onset of Alzheimer's disease in the subject.

This invention provides a method of enhancing growth of a neuron which comprises contacting the neuron with: (a) estrogen in an amount effective to increase the level of neurotrophin receptors and (b) a neurotrophin in an amount effective to increase the level of estrogen receptors, so as to enhance growth of the neuron.

This invention provides a method for enhancing regeneration of a neuron which comprises contacting the neuron with: (a) estrogen in an amount effective to increase the level of neurotrophin receptors and (b) a neurotrophin in an amount effective to increase the level of estrogen receptors, so as to enhance regeneration of the neuron.

This invention provides a method of repairing injured neurons, which comprises contacting the injured neurons with: (a) estrogen in an amount effective to increase the level of neurotrophin receptors and (b) a neurotrophin in an amount effective to increase the level of estrogen receptors, so as to repair the injured neurons.

BRIEF DESCRIPTION OF THE FIGURES

First Series of Experiments

FIGS. 1A–1C: Estrogen receptor mRNA expression in PC12 cells.

Figure 4A:
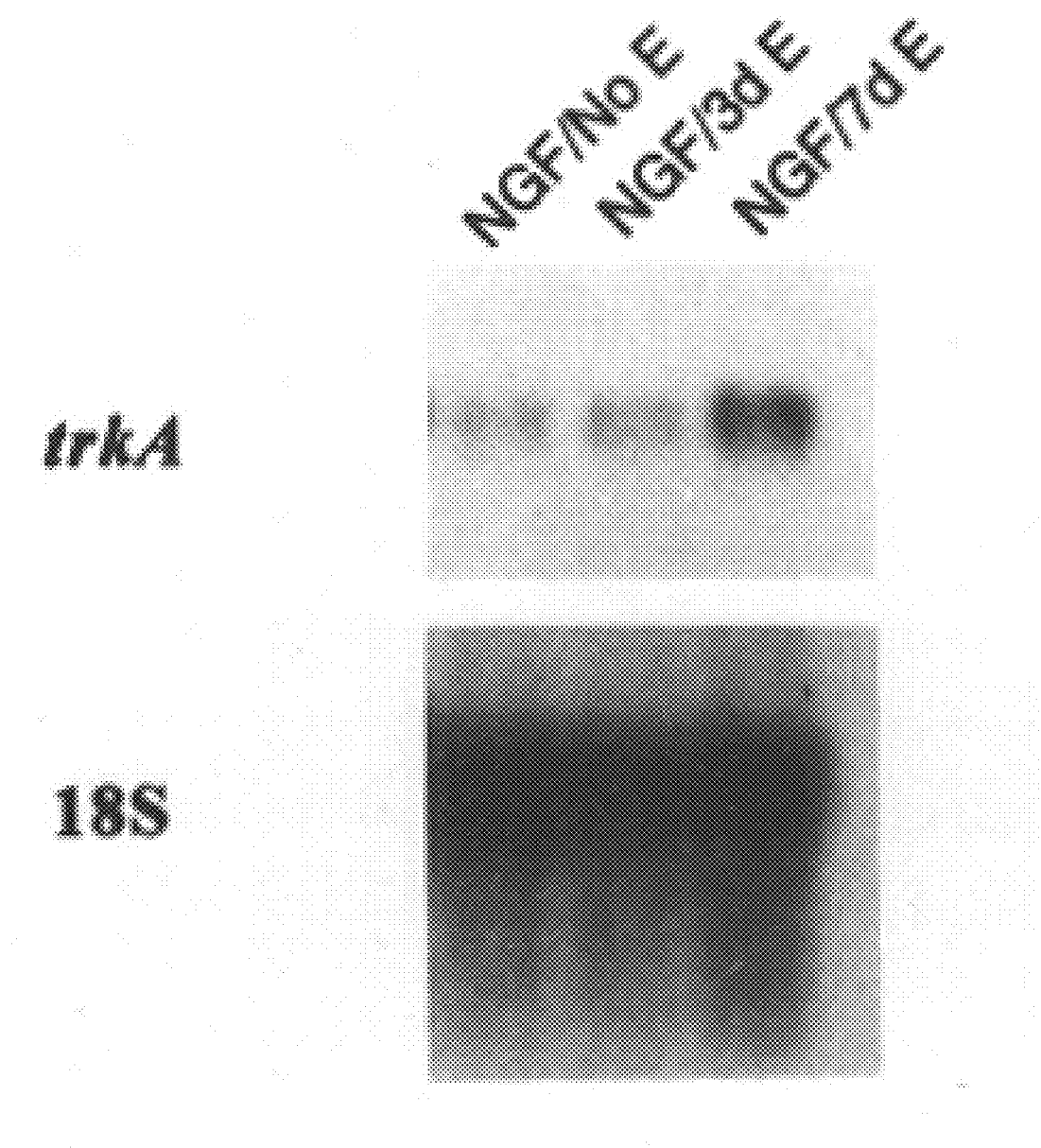

Naive and NGF-treated (14 days) PC12 cells grown on coverslips were hybridized to a 48 base digoxigenin-labeled oligonucleotide probe for the estrogen receptor. While a few scattered cells stain darkly (FIGS. 1A and 1C), the majority of naive PC12 cells appear to hybridize this probe minimally (FIG. 1C) or not at all (FIG. 1A). Virtually all PC12 cells in the NGF-treated group (FIG. 1B), however, strongly hybridize with the estrogen receptor probe. (Bar=50 mm)

FIG. 2: Estrogen receptor MRNA analysis by RT-PCR.

Estrogen receptor mRNA from naive and NGF-treated (14 days) PC12 cells was reverse transcribed using primers from the ligand binding domain of this receptor. The amplified product shows the expected 300 (odd-numbered lanes) and 200 (even-numbered lanes) base pair bands in both naive (lanes 5,6) and NGF-treated (lanes 7,8) PC12 cell RNA. Similar sized bands were also seen in reverse-transcribed rat uterine RNA (lanes 3,4). No bands were seen in reverse transcribed yeast RNA (lane 9), which does not have the estrogen receptor, or in samples where no RNA was present (lane 2). Lanes 1 and 10 are DNA size markers.

FIGS. 3A–3B: Nuclear estrogen binding by PC12 cells.

FIG. 3A: While specific nuclear estrogen-binding was present in both naive (No NGF/No E) and NGF-treated PC12 cells, estrogen binding was enhanced 6-fold in PC12 cells exposed to NGF for 3 weeks (NGF (21d); *=p<0.05). Estrogen binding was decreased in NGF-treated cells exposed concurrently to estrogen (NGF (21d) +E (7d)), as compared to NGF treatment alone (**=p<0.05). The means (+SEM) of three independent experiments are shown.

FIG. 3B: Time course study of nuclear estrogen binding by PC12 cells in response to NGF exposure indicates that NGF-induced increase in estrogen binding is present as early as 4 days after neurotrophin treatment. (Mean values for 1, 4, and 7 days of NGF treatment are derived from duplicate determinations of one experiment; error bars indicate range of values).

Figure 4B:
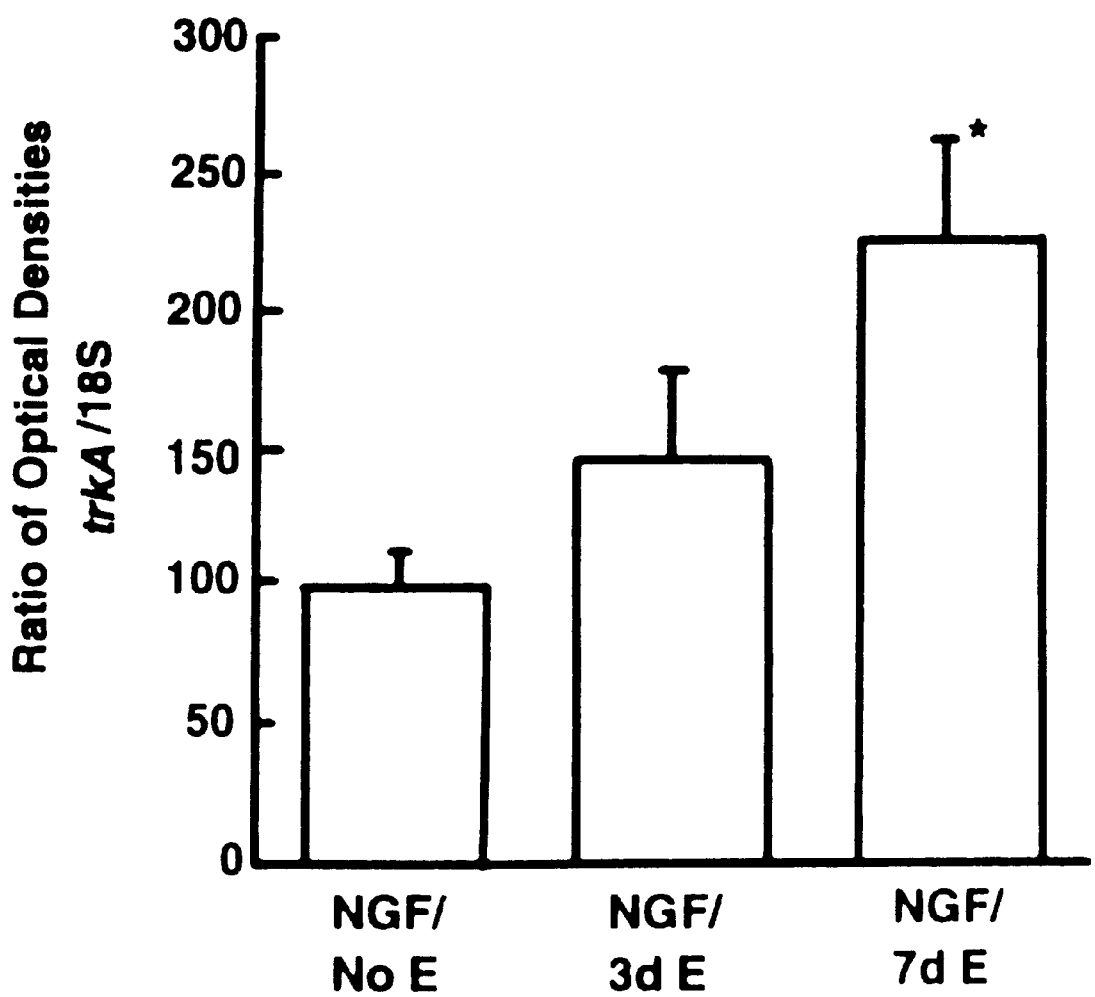

FIGS. 4A–4B: Effect of estrogen on trkA mRNA.

FIG. 4A: Total RNA, obtained from NGF-treated (NGF/No E), NGF and 3 day estrogen-treated (NGF/3d E) and NGF and 7 day estrogen-treated (NGF/7d E) PC12 cells, loaded 10 mg per lane, was hybridized to a 32P-labeled, 450 bp cDNA probe for trkA MRNA (pDM97; gift of L. F. Parada) [67]. Note that while 3 days of estrogen treatment did not visibly alter trkA mRNA from basal levels, the level of this transcript increased two-fold after 7 days of estrogen treatment.

FIG. 4B: To quantify group differences, optical density of the trkA transcript was normalized to 18S ribosomal RNA, to control for variations in the amount of total RNA loaded onto the gel. Bar graph represents mean (+SEM) of 5–6 replicates across 2–3 independent experiments. * indicates $p<0.05$.

Figure 5B:
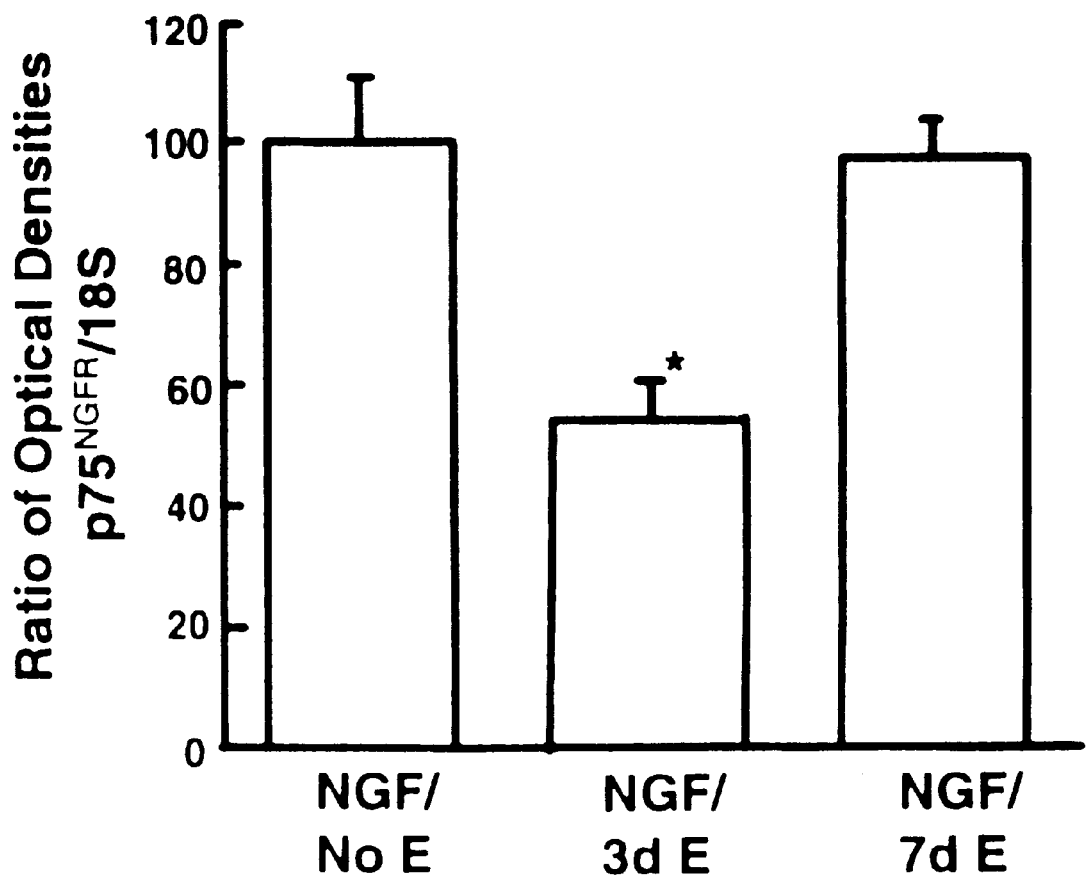

FIGS. 5A–5B: Effect of estrogen on p75NGFR mRNA.

FIG. 5A: Total RNA, obtained from NGF-treated (NGF/No E), NGF and 3 day estrogen-treated (NGF/3d E) and NGF and 7 day estrogen-treated (NGF/7d E) PC12 cells, loaded 10 mg per lane, was hybridized to a 32P-labeled, 2 Kb cDNA probe for p75NGFR (p5b). Note that p75NGFR mRNA decreased by half in cells concurrently exposed to estrogen and NGF for 3 days as compared to those treated with NGF alone, but was no different from basal levels after 7 days of estrogen treatment.

FIG. 5B: To quantify group differences, optical density of p75NGFR transcript was normalized to 18S ribosomal RNA, to control for variations in the amount of total RNA loaded onto the gel. Bar graph represents mean (+SEM) of 5–6 replicates across 2–3 independent experiments. * indicates $p<0.05$.

Second Series of Experiments

FIG. 6A–D.

(a,b) Hemicoronal, organotypic explant cultures of postnatal day 2 rat (a) cerebral cortex and (b) basal forebrain maintained for 8 days in vitro in roller tube assemblies. (c,d) Estrogen receptor-like immunoreactive product is localized to nuclei of cells in (c) a whole-mount explant culture of the cerebral cortex as compared to the lack of staining in (d) preimmune serum control cultures. (d) Photomicrograph was obtained using differential interference contrast photomicrography to highlight the unstained cells. Scale bar100 μm. Abbreviations; nu, neurite; cp, cortical plate; cc corpus callosum; ms, medial septum; ls, lateral septum; vdb; vertical limb, diagonal band of Broca; hbd, horizontal limb, diagonal band of Broca.

FIG. 7: Expression of TrkA protein in explant cultures of the cerebral cortex was detected by Western analysis.

Immunoprecipitates of pooled cortical explants (three explants/sample) maintained for 8 days in vitro were size fractionated, transferred to nitrocellulose, and probed for the specific expression of TrkA. TrkA signal (a band at ~140 kDa, arrow) was present in both explant cultures (lanes 2–5) and PC12 cells (a positive control, lane 6) but not in the negative control (lane 7, PC12-NNR5 cells, a PC12 cell subclone that is TrkA deficient).

FIG. 8.

Specific nuclear [$^3$H]moxestrol binding (normalized to DNA content) was observed in both cortical and basal forebrain explant cultures maintained for 8 days in vitro. The addition of hrNGF led to a significant increase(*) in nuclear estrogen binding sites in cortical but not basal forebrain explant cultures. n=sample size in each of the groups.

FIGS. 9A–B.

Estrogen receptor mRNA expression in explant cultures of the cerebral cortex and basal forebrain was measured by semiquantitative RT-PCR and normalized to a concurrently reverse transcribed and amplified internal control (cyclophilin mRNA). Each cortical sample consisted of two pooled cultures, and each basal forebrain sample consisted of four pooled cultures. (a) Photomicrograph of $^{32}$P-labeled RT-PCR products from cortical explant cultures maintained in the presence (+NGF) or absence (−NGF)of hrNGF, size fractionated on a nondenaturing polyacrylamide gel. The upper photomicrograph shows the presence of a 300-bp fragment, identical to a region within rat estrogen receptor mRNA, coding for the ligand binding domain. The lower photomicrograph shows the corresponding expression of cyclophilin mRNA. (b) Densitometric analysis of the expression of estrogen receptor mRNA (normalized to cylophilin mRNA) in pooled samples of cortical and basal forebrain explant cultures. The addition of exogenous hrNGF did not lead to an alteration in estrogen receptor mRNA levels. n=sample size in each of the conditions, and numbers in brackets indicate the total number of cultures assigned to each group.

Figure 10:
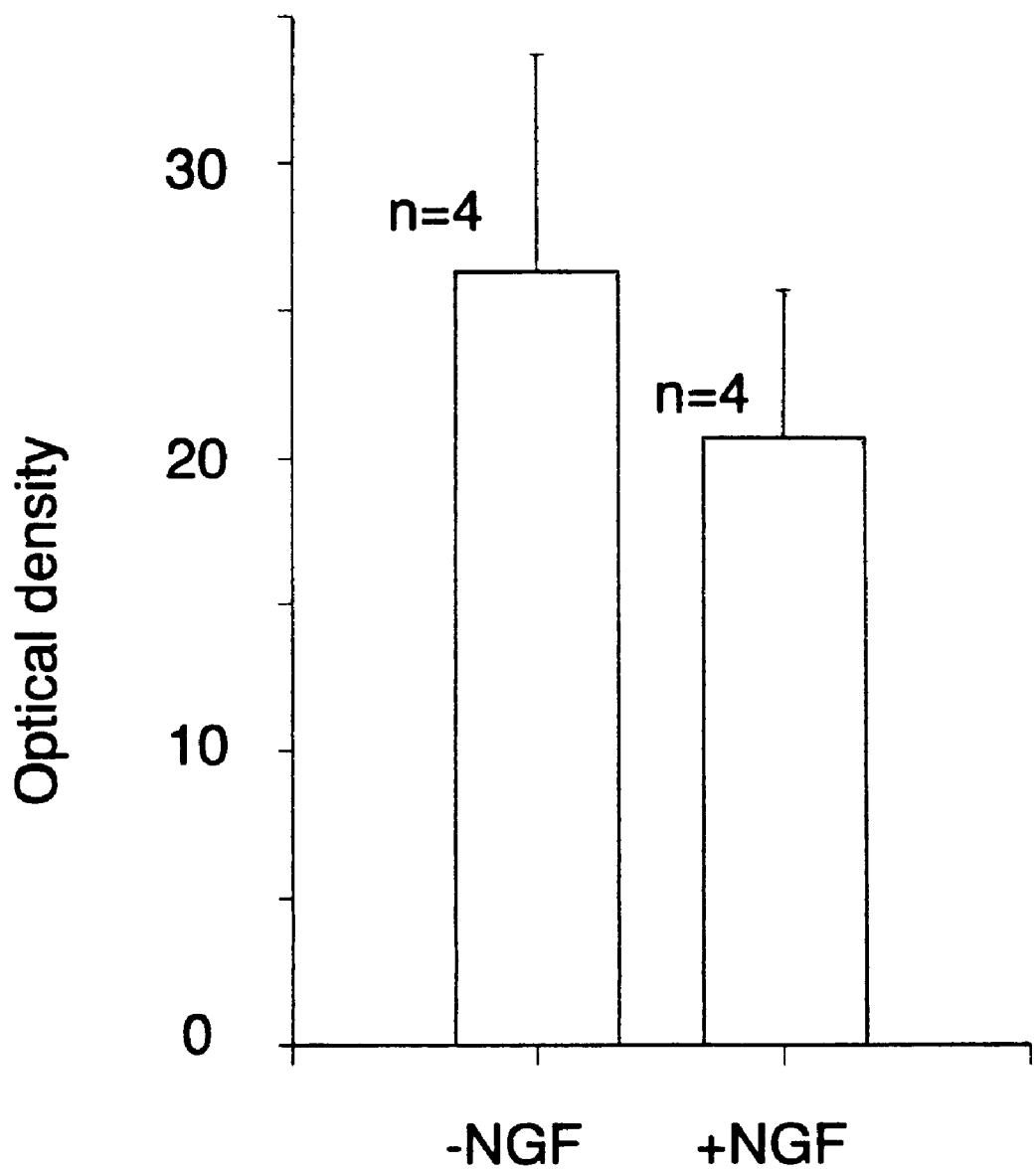

FIG. 10. Densitometric analysis of estrogen receptor mRNA expression in explant cultures of the cerebral cortex using isotopic in situ hybridization.

The addition of hrNGF to cortical explant cultures did not lead to an alteration in estrogen receptor mRNA levels.

DETAILED DESCRIPTION OF THE INVENTION

This invention provides a method of increasing the level of estrogen receptors in a sample of neural tissue from a subject which comprises contacting the sample with: (a) estrogen in an amount effective to increase the level of neurotrophin receptors and (b) a neurotrophin in an amount effective to increase the level of estrogen receptors, so as to thereby increase the level of estrogen receptors in the neural tissue.

In an embodiment, the neurotrophin receptors are selected from a group consisting of trkA receptors, trkB receptors, and trkC receptors. In a further embodiment, the neurotrophin is a nerve growth factor.

In an embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5). In a further embodiment, the neurotrophin and estrogen are administered concurrently. In a still further embodiment, the neurotrophin and estrogen are administered separately.

This invention provides a method of triggering gene regulation in a sample of neural tissue of a subject which comprises contacting the sample with (a) estrogen and (b) neurotrophin in effective amounts to induce tyrosine phosphorylation of the estrogen receptors and tyrosine phosphorylation of the neurotrophin receptors so as to trigger gene regulation.

In an embodiment, the neurotrophin receptors are selected from a group consisting of trkA receptors, trkB receptors, and trkC receptors. In a further embodiment, the neurotrophin is a nerve growth factor. In an embodiment, he neurotrophin is selected from a group consisting of human recombinant nerve growth factor (NGF), brain-derived neurotrophic factor (BDNF), neurotrophin-3 (NT-3), and neurotrophin-4/5 (NT-4/5). In a further embodiment the neurotrophin and estrogen are administered concurrently. In a further embodiment, the neurotrophin and estrogen are administered separately.

This invention provides a method of increasing the level of estrogen receptors in neural tissue of a subject which comprises administering to the subject: (a) estrogen in an amount effective to increase the level of neurotrophin receptors and (b) a neurotrophin in an amount effective to increase the level of estrogen receptors, so as to thereby increase the level of estrogen receptors.

In an embodiment, the neurotrophin receptors are selected from a group consisting of trkA receptors, trkB receptors, and trkC receptors. In a further embodiment, the neurotrophin is a nerve growth factor.

In an embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5). In a further embodiment, the neurotrophin and estrogen are administered concurrently. In an embodiment, the neurotrophin and estrogen are administered separately.

In a further embodiment the effective amount of (a) estrogen and (b) neurotrophin induces tyrosine phosphorylation of the estrogen receptors and the effective amount of (a) estrogen induces tyrosine phosphorylation of the neurotrophin receptors.

This invention provides a method of increasing the level of estrogen receptors in neural tissue of a subject which comprises administering to the subject: (a) estrogen in an amount effective to increase the level of neurotrophin receptors and (b) a neurotrophin conjugated to an antibody in an amount effective to increase the level of estrogen receptors, so as to thereby increase the level of estrogen receptors.

In an embodiment, the neurotrophin receptors are selected from a group consisting of trkA receptors, trkB receptors, and trkC receptors. In a further embodiment, the neurotrophin is a nerve growth factor. In another embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5).

In an embodiment, the neurotrophin and estrogen are administered concurrently. In a further embodiment, the neurotrophin and estrogen are administered separately. In an embodiment, the effective amount of (a) estrogen and (b) neurotrophin induces tyrosine phosphorylation of the estrogen receptors and the effective amount of (a) estrogen induces tyrosine phosphorylation of the neurotrophin receptors.

This invention provides a method of preventing the onset of Alzheimer's disease in a subject which comprises administering to the subject: (a) estrogen in an amount effective to increase the level of neurotrophin receptors and (b) a neurotrophin in an amount effective to increase the level of estrogen receptors, so as to thereby prevent the onset of Alzheimer's disease in the subject.

In an embodiment, the neurotrophin receptors are selected from a group consisting of trkA receptors, trkB receptors, and trkC receptors. In another embodiment, the neurotrophin is a nerve growth factor. In an embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5). In an embodiment, the neurotrophin and estrogen are administered concurrently. In another embodiment, the neurotrophin and estrogen are administered separately. In another embodiment, the effective amount of (a) estrogen and (b) neurotrophin induces tyrosine phosphorylation of the estrogen receptors and the effective amount of (a) estrogen induces tyrosine phosphorylation of the neurotrophin receptors.

This invention provides a method of preventing the onset of Alzheimer's disease in a subject which comprises administering to the subject: (a) estrogen in an amount effective to increase the level of neurotrophin receptors and (b) a neurotrophin conjugated to an antibody in an amount effective to increase the level of estrogen receptors, so as to thereby prevent the onset of Alzheimer's disease in the subject.

In an embodiment, the neurotrophin receptors are selected from a group consisting of trkA receptors, trkB receptors, and trkC receptors. In another embodiment, the neurotrophin is a nerve growth factor. In a further embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5). In an embodiment, the neurotrophin and estrogen are administered concurrently. In another embodiment, the neurotrophin and estrogen are administered separately. In an embodiment, the effective amount of (a) estrogen and (b) neurotrophin induces tyrosine phosphorylation of the estrogen receptors and the effective amount of (a) estrogen induces tyrosine phosphorylation of the trkA receptors.

This invention provides a method of enhancing growth of a neuron which comprises contacting the neuron with: (a) estrogen in an amount effective to increase the level of neurotrophin receptors and (b) a neurotrophin in an amount effective to increase the level of estrogen receptors, so as to enhance growth of the neuron.

As used herein, a neuron is comprised of axons, dendrites and synapses.

In an embodiment, the neurotrophin receptors are selected from a group consisting of trkA receptors, trkB receptors, and trkC receptors. In another embodiment, the neurotrophin is a nerve growth factor. In a further embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5). In an embodiment, the neurotrophin and estrogen are administered concurrently. In another embodiment, the neurotrophin and estrogen are administered separately.

This invention provides a method for enhancing regeneration of a neuron which comprises contacting the neuron with: (a) estrogen in an amount effective to increase the level of neurotrophin receptors and (b) a neurotrophin in an amount effective to increase the level of estrogen receptors, so as to enhance regeneration of the neuron.

In an embodiment, the neurotrophin receptors are selected from a group consisting of trkA receptors, trkB receptors, and trkC receptors. In another embodiment, the neurotrophin is a nerve growth factor. In a further embodiment, the neurotrophin is selected from a group consisting of human recombinant nerve growth factor (NGF), brain-derived neurotrophic factor (BDNF), neurotrophin-3 (NT-3), and neurotrophin-4/5 (NT-4/5). In an embodiment, the neurotrophin and estrogen are administered concurrently. In another embodiment, the neurotrophin and estrogen are administered separately.

This invention provides a method of repairing injured neurons, which comprises contacting the injured neurons with: (a) estrogen in an amount effective to increase the level of neurotrophin receptors and (b) a neurotrophin in an amount effective to increase the level of estrogen receptors, so as to repair the injured neurons.

Estrogens are steroid hormones which act by regulating transcription of a variety of proteins: steroid, peptide, and neurotransmitter receptors, also hormones and neuropeptides. The hormones diffuse passively through cell membranes, distribute themselves throughout the cell, and ultimately bind to a nuclear estrogen receptor protein. The estrogen receptor protein, found in estrogen-responsive tissues, is a DNA binding protein that is homologous with the receptors for other steroid hormones, vitamin D, retinoic acid, and the thyroid hormones. Once activated by ligand, the estrogen receptor binds to specific DNA sequences and regulates their transcription [113].

Estrogen molecules are 18-carbon steroids containing a phenolic A ring and a β-hydroxyl group or ketone in position of ring D. The phenolic A ring is the principal structural feature responsible for selective, high-affinity binding to estrogen receptors. Most alkyl substitutions on the phenolic A ring impair such binding, but substitutions on ring C or D may be tolerated [113]. Steroidal estrogens include, but are not limited to, estradiol, estron, and estriol. In the preferred embodiment the estrogen is estradiol. In another embodiment the estrogen may contain substitutions on ring C or D.

Nonsteroidal compounds with estrogenic activity occur naturally in a variety of plants, including flavone, isoflavone, and coumestan derivatives (phytoestrogens) [113]. Many of these polycyclic compounds contain a phenolic ring that mimics the A ring of steroids. Since the phenolic A ring is the principal structural feature responsible for selective, high-affinity binding to estrogen receptors, these nonsteroidal compounds are capable of binding to estrogen receptors. In another embodiment, the estrogen may be substituted with a nonsteroidal compound with estrogenic activity, for example, diethylstilbestrol.

In this invention, estrogen receptor levels are increased by administering estrogen and neurotrophin to neural tissue. Neural tissue is comprised of neurons. Examples of neural tissue include, but are not limited to, the brain and spinal cord. The brain and spinal cord are composed of a network of neurons among supporting glial cells. In the preferred embodiment, the neural tissue is brain tissue.

Estrogen is administered to neural tissue in combination with a neurotrophin, such as nerve growth factor, in order to increase the level of estrogen receptors in neural tissue. The administration of estrogen to the neural tissue increases the level of trkA receptors. trkA receptors are receptors for neurotrophins. The administration of neurotrophin to the neural tissue increases the level of estrogen receptors. This reciprocal regulation of NGF receptors and estrogen receptors thereby increases the level of estrogen receptors in neural tissue.

Estrogen has various beneficial effects in neural tissue. For example, estrogen effects changes in neurons and in neurotransmitters. Estrogen affects neuronal structure, physiology and gene expression in specific adult steroid targets [19, 21, 30, 68, 83]. Estrogen also regulates transcription of a variety of structural proteins [38, 62, 94], steroid, peptide and neurotransmitter receptors [19, 21, 63], as well as hormones and neuropeptides [83, 110].

Estrogen and neurotrophin are administered in effective amounts. Precise amounts of active ingredients required to be administered depend on the judgment of the practitioner and are peculiar to each sample.

In one embodiment, the dosage of estrogen effective to increase the level of trkA receptors in a sample is in the range of $1\times10^{-9}$ M 17-β estradiol to $5\times10^{-9}$ M 17-β estradiol. In another embodiment, the dosage is $2\times10^{-9}$ M 17-β estradiol. In one embodiment the dosage of estrogen is administered in the range of 1 to 21 days. In the preferred embodiment the dosage is administered for 4 to 7 days.

The base level of trkA mRNA in neural tissue is measured in the range of 80–120 as the ratio of optical density of trkA/18S. trkA mRNA levels increase twofold by 7 days of estrogen treatment.

Neurotrophins are a class of proteins which control nerve cell growth and survival. The neurotrophin family of growth factors share marked similarities in their conserved sequences and structural domains. Ligand specificity and signal transduction requires the neurotrophins to associate with members of the trk proto-oncogene receptor tyrosine kinase family of membrane bound receptors [48, 53, 91, 92]. The neurotrophins include, but are not limited to nerve growth factor [55], brain derived neurotrophic factor, neurotrophin-3 and neurotrophin-4/5 [2, 12, 47, 65, 81]. In the preferred embodiment, the neurotrophin is nerve growth factor.

In one embodiment the dosage level of neurotrophin effective to increase the level of estrogen receptors in culture is in the range of 1–200 ng/ml. In another embodiment the dosage level is 10–100 ng/ml. In a preferred embodiment the dosage level is 30–70 ng/ml.

The base level of estrogen binding in neural tissue is in the range of 1–6 fmols/mg DNA. Estrogen binding levels double by 4 days of nerve growth factor treatment and increase sixfold following 21 days of treatment.

In one embodiment the neurotrophin and estrogen are administered concurrently. In another embodiment the neurotrophin and estrogen are administered separately.

This invention also provides a method of increasing the level of estrogen receptors in neural tissue of a subject which comprises administering to the subject estrogen in an amount effective to increase the level of trkA receptors and a neurotrophin in an amount effective to increase the level of estrogen receptors, so as to thereby increase the level of estrogen receptors.

As used herein, a subject may be a mammal, or more specifically, a human, horse, pig, rabbit, dog, monkey, or rodent. In the preferred embodiment the subject is a human.

As used herein administration means a method of administering to a subject. Such methods are well known to those skilled in the art and include, but are not limited to, administration topically, parenterally, orally, intravenously, intramuscularly, subcutaneously or by aerosol. Administration of estrogen may be effected continuously or intermittently such that the therapeutic agent in the subject is effective to increase the level of trkA receptors in neural tissue. In the preferred embodiment, estrogen is administered to subjects orally in a pharmaceutically acceptable carrier.

In the preferred embodiment, standard oral dosage levels of estrogen are administered. The dosage range of estrogen effective to increase the level of trkA receptors is in the range of 0.01 to 10 mg. In another embodiment, the dosage range is 0.3 to 2.5 mg.

Neurotrophins generally can not be administered to a subject via the bloodstream, because neurotrophins do not significantly penetrate the blood-brain barrier [114]. Therefore neurotrophins must be administered locally.

In one embodiment the neurotrophin is administered via genetically engineered cells which are encapsulated and implanted into the brain or injected in the ventricles.

In another embodiment the neurotrophin is administered via a brain pump which releases the neurotrophin into neural tissue or in cavities called ventricles.

This invention further provides a method of increasing the level of estrogen receptors in neural tissue of a subject which comprises administering to the subject estrogen in an amount effective to increase the level of trkA receptors and a neurotrophin conjugated to an antibody in an amount effective to increase the level of estrogen receptors, so as to thereby increase the level of estrogen receptors.

As used herein, a neurotrophin is conjugated to an antibody to the transferrin receptor. In a preferred embodiment the neurotrophin is linked in a biologically active form to an OX-26 antibody, which is an antibody against the rat transferrin receptor.

In a preferred embodiment the neurotrophin is nerve growth factor. In the preferred embodiment, OX-26-NGF conjugates are synthesized by introduction of a protected sulfhydryl group onto the antibody to the transferrin receptor through lysine E-amines and the introduction of a heterobifunctional cross-linker that contains a thiol reactive group onto NGF through carboxyl groups [114].

Estrogen affects certain diseases in neural tissue. Diseases which may be prevented or treated by increasing the level of estrogen receptors in neural tissue include, but are not limited to, Alzheimer's disease, cognitive disorders associated with aging, and all types of brain injury.

This invention provides a method of preventing the onset of Alzheimer's disease in a subject which comprises administering estrogen to the neural tissue in an amount effective to increase the level of trkA receptors, and administering neurotrophin in an amount effective to increase the level of estrogen receptors, thereby preventing the onset of Alzheimer's disease in the subject.

Alzheimer's disease is a type of dementia due to a degenerative process, with a loss of cells from the basal forebrain, cerebral cortex, and other brain areas [115]. Acetylcholine-transmitting neurons and their target nerve cells are particularly affected.

Cholinergic neurons in the basal forebrain have estrogen receptors. Cholinergic neurons use acetylcholine as a transmitter and are among the first neurons to die or shrink with Alzheimer's.

In the preferred embodiment of the method of preventing the onset of Alzheimer's disease in a subject the neurotrophin is nerve growth factor.

Lastly, this invention provides a method of preventing the onset of Alzheimer's disease in a subject which comprises administering estrogen to the neural tissue in an amount effective to increase the level of trkA receptors, and administering neurotrophin conjugated to an antibody to the transferrin receptor in an amount effective to increase the level of estrogen receptors, thereby preventing the onset of Alzheimer's disease in the subject.

This invention is further illustrated in the Experimental Details section which follows. This section is set forth to aid in an understanding of the invention but is not intended to, and should not be construed to, limit in any way the inventions as set forth in the claims which follow thereafter.

First Series of Experiments

EXPERIMENTAL DETAILS

I. Materials and Methods

Tissue Culture:

PC12 cells were cultured on collagen-coated coverslips or tissue culture dishes in phenol red-free RPMI 1640 (Gibco BRL) nutrient medium supplemented with 10% (heat-inactivated) gelded (steroid-deficient) horse serum (JRH Biological), according to a modification of standard procedures [37]. In these experiments, fetal calf serum, which contains physiologic levels of estrogen, (32 pg/ml) was not used. NGF-treated groups were primed for 2–3 weeks in the presence of 50 ng/ml NGF, and estrogen-treated groups were exposed to $2 \times 10^{-9}$ M 17-β estradiol (Sigma) for periods ranging from 1 to 7 days.

In situ hybridization:

Estrogen receptor mRNA was identified using a previously described [71] unique 48-base oligonucleotide sequence, identical to a region within the ligand-binding domain of the rat uterine estrogen receptor [51] and with less than 25% homology with the other members of the steroid receptor superfamily of DNA binding proteins. The probes were 3' end-labeled with digoxigenin-deoxyuridine-triphosphate using terminal deoxynucleotidyl transferase (BRL) [71, 106].

In situ hybridization histochemistry for the estrogen receptor was performed according to the procedure described in Miranda and Toran-Allerand [71]. Briefly, paraformaldehyde-fixed cultures were hybridized with digoxigenin-labeled oligonucleotide for 16–18 hours, washed extensively and later incubated with antidigoxigenin antibody conjugated to alkaline phosphatase (Boehringer Mannheim). RNA-oligonucleotide hybrids were visualized with a blue color reaction (nitroblue tetrazolium salt/5-bromo-4-chloro-3-indolyl-phosphate) catalyzed by antibody-conjugated alkaline-phosphatase. Color reaction was terminated for all groups when color appeared fully developed in one condition. Coverslips were dehydrated briefly, cleared in Histoclear (National Diagnostics) and coverslipped in Permount. Hybridization and immunohistochemical controls for the estrogen receptor oligonucleotide are described in the Results; extensive controls ensuring the specificity of the non-isotopic in situ hybridization method and the probe used here are described in Miranda and Toran-Allerand [71] and Toran-Allerand and Miranda [104].

Northern Blot Analysis:

Total RNA, prepared by a modification [58] of the Chomczynski and Sacchi [13] method, was size-fractionated (10–20 μg/lane) on a 1.2% agarose-18% formaldehyde gel and capillary-transferred to nylon membrane (Hybond-N; Amersham). Filters were prehybridized (4–18 h) and hybridized (36–40 h) at 42° C. in 50% Formamide, 3× SSC, 0.1M Tris, 5× Denhardt's and 10% Dextran Sulfate. Probes were labeled with [α-$^{32}$P]-dCTP by the random priming procedure (Random Priming kit, Boehringer Mannheim). trkA mRNA was identified by hybridization with pDM97, a 450 bp trkA-specific probe corresponding to the extracellular and transmembrane domains of the trkA gene [67; gift of L. F. Parada, NCI-FCRDC]. $p75^{NGFR}$ was probed by hybridization with p5b, a 2 Kb probe corresponding to the extracellular domain of the $p75^{NGFR}$ gene [9]. Blots were washed first in 0.2×SSC and 0.5% SDS briefly at room temperature and then for 2 h at 60° C., with frequent changes of wash buffer. Filters were then exposed to film (Kodak X-Omat) between intensifying screens and stored at –70° C. for 1–4 days before developing.

Using a standard densitometry package (Jandel Scientific), optical density measurements were obtained from X-ray film. trkA and $p75^{NGFR}$ transcript densities were normalized to an internal control to account for variation in the amount of RNA loaded. Since both estrogen and NGF have been reported to enhance the expression of commonly used controls such as β-actin [38, 42] and gonadal steroids have been shown to regulate 28S, but not 18S, ribosomal RNA [112], NGF receptor transcripts in this study were normalized to 18S ribosomal RNA bands, visualized by an 18S-specific riboprobe (Ambion, Tex.).

Estrogen Receptor Binding Assay:

Estrogen binding was estimated by a modification [90] of the nuclear exchange assay [64]. PC12 cells were grown as above and exposed to one of three feeding paradigms: no NGF/no estradiol; 3 wks NGF/no estradiol; and 2 weeks NGF/1 week NGF+$10^{-9}$M estradiol. Groups receiving estrogen were deprived of the steroid 24 h prior to the assay. For the assay, half the cultures in each group were exposed to nutrient medium (phenol red-free RPMI+10% gelded horse serum) containing 2 nM [$^{3}$H]-Moxestrol (R2858; Dupont NEN; specific activity 80 Ci/mmol) and the other half exposed to the radioligand in the presence of 2 μM of (unlabeled) diethylstilbestrol (DES), a non-steroidal synthetic estrogen. As a control, some dishes were exposed to 2 nM [$^{3}$H]-Moxestrol with 2 μM 5α-dihydrotestosterone (DHT), a non-aromatizable androgen. Following incubation at 34° C. for 2 h, all subsequent procedures were carried out at 4° C. Radioactive medium was removed by aspiration, and the cultures bathed in buffer containing 1 mM potassium phosphate, 3 mM magnesium chloride and 0.25% Triton X-100 (pH 6.5). Cells were gently scraped and collected, with buffer, into 1.5 ml microcentrifuge tubes. Tubes were then centrifuged briefly (5 mins, 14000 g) to recover a pellet and washed (3×) in the same buffer, excluding Triton X. Since the estrogen receptor is a nuclear receptor, in some experiments a sucrose gradient protocol [64] was employed to ensure a clean nuclear pellet. In this case, cells were scraped in a similar buffer as before, with the addition of 1.36 M sucrose. This mixture was then carefully layered over a buffer containing 1.8 M sucrose and centrifuged for 90 mins, at 15,000 g at 4° C., and the nuclear pellet recovered from the bottom of the tube. Radioactivity was then eluted from the pellet (obtained by either method) by washing with 1 ml of 95% ethanol (estrogen is completely soluble in >50% ethanol), and the radioactivity counted in a liquid scintillation counter. Pellets were then dried and resuspended in 1xTES (0.1M Tris, 0.01M EDTA, 0.1% SDS) and assayed fluorometrically for DNA content, using the Hoechst dye #33258 [11]. Specific binding was determined as the difference between total binding and non-specific binding (in the presence of an unlabeled competing ligand). On average, specific binding was 44% of total binding. Group differences were evaluated using one way analysis of variance with Student-Newman-Keuls test of planned post-hoc comparisons. Differences were considered significant at the 0.05 level.

Reverse Transcriptase-Polymerase Chain Reaction (RT-PCR):

Estrogen receptor mRNA was detected by RT-PCR, using the GeneAmp kit (Perkin-Elmer Cetus), according to the manufacturer's instructions. Using 1–2 mg of total RNA, first strand synthesis (or template cDNA) was primed by random hexamers in the presence of 5 mM MgCl2, 1 mM dNTPs and 2.5U/μl Reverse Transcriptase, in buffer containing 50 mM KCl and 10 mM Tris-HCl. The mixture was incubated at 42° C. for 45 mins and terminated by heat-denaturing (99° C. for 5 mins).

For PCR amplification, the reaction volume was increased to 100 μl in the same buffer, with MgCl2 concentration adjusted to 2 mM, and the addition of 2.5 U/100 ml of DNA polymerase (AmpliTaq, Perkin Elmer Cetus). Forward and reverse primers for the estrogen receptor, from the region coding the ligand-binding domain (gift of Dr. B. Schachter, Mount Sinai Medical School), were added at a final concentration of 0.6 μM. Tubes were layered with oil (Mineral oil, Sigma) and cycled (20–35×) through the following program: 94° C. for 30 secs, 40° C. for 30 sec, 75° C. for 75 secs. The mineral oil was removed by chloroform extraction, the reaction mixture precipitated, and the pellet resuspended in water. The reverse-transcribed, amplified product was size-fractionated on a 2.5% agarose (electrophoresis grade; or 0.6% low melt grade agarose)-ethidium bromide gel and photographed under UV illumination. Low-melt agarose plugs containing the 200 base pair product were phenol-purified, sub-cloned into a direct cloning vector (pGEM-t; Promega) and transfected into competent cells (DH5α; Gibco BRL), and the product was sequenced on a BioSystem sequence analyzer (DNA Facilities, HHSC, Columbia University).

II. Results

This invention discloses the potential for reciprocal regulation of estrogen and neurotrophin receptor systems by their ligands in a prototypical neurotrophin target, the PC12 cell, was examined. Using in situ hybridization histochemistry, RT-PCR and a modified nuclear exchange assay, both estrogen receptor mRNA and estrogen binding in PC12 cells were found. Moreover, while estrogen binding was relatively low in naive PC12 cells, long-term exposure to NGF enhanced estrogen binding in these cells by six-fold. Furthermore, concurrent exposure to estrogen and NGF differentially regulated the expression of the two NGF receptor mRNAs. The expression of trkA mRNA was up-regulated while $p75^{NGFR}$ mRNA was down-regulated transiently. The present data indicate that NGF may increase neuronal sensitivity to estrogen, and that estrogen, by differentially regulating $p75^{NGFR}$ and trkA mRNA, may alter the ratio of the two NGF receptors, and, consequently, neurotrophin responsivity. In view of the widespread co-localization of estrogen and neurotrophin receptor systems in the developing CNS, the reciprocal regulation of these receptor systems by NGF and estrogen may have important implications for processes governing neural maturation and the maintenance of neural function.

Estrogen receptor MRNA is expressed in PC12 cells:

Both naive (NGF-untreated) and NGF-treated PC12 cells express MRNA for the estrogen receptor. In situ hybridization histochemistry, using a 48 base oligonucleotide probe for this receptor, revealed hybridization product in PC12 cells, both before and after long-term (>2 weeks) exposure to NGF (FIG. 1A–1C). In naive PC12 cells, the extent and pattern of hybridization was heterogenous (FIGS. 1A and 1C). In all instances, a few scattered cells in the population strongly hybridized the estrogen receptor (FIGS. 1A and 1C). However, the majority of naive PC12 cells frequently had no (FIG. 1A) or, in some cases, low (FIG. 1C) hybridization signal. In contrast, virtually all PC12 cells in the NGF-treated condition strongly hybridized the estrogen receptor probe (FIG. 1B). Typically, hybridization was restricted to the cytoplasm. The alkaline phosphatase product, however, is flocculent, and, where the probe hybridizes abundantly, as in FIG. 1B, overstaining occasionally led to color diffusion into neurites.

The estrogen receptor probe used here is highly specific for the estrogen receptor and, by Northern analysis, recognizes a band of approximately 6.5 Kb in rat uterine RNA [71]. To ensure that the reaction product was the result of specific hybridization to the oligonucleotide, some cultures were incubated with the estrogen receptor probe after prior incubation in a 100-fold excess of an unlabeled, 90 base oligonucleotide (deduced amino acids 564–593) that completely overlapped the 48 base experimental probe. These sections always remained unstained. As an immunohistochemical control, additional cultures were hybridized with a non-complementary ('sense') oligonucleotide, and these sections also remained unstained.

In situ expression of estrogen receptor MRNA in PC12 cells was corroborated using RT-PCR. RNA from untreated (FIG. 2, lanes 5,6) and NGF-treated PC12 cells (FIG. 3, lanes 7,8), primed and amplified with 2 sets of primers specific for the rat estrogen receptor, revealed bands of 300 and 200 base pairs. Based on the sequenced rat uterine estrogen receptor, both products were of the expected size. The 200 bp PCR product from NGF-treated PC12 cell RNA was subcloned and sequenced, and found to be identical to the appropriate domain within the sequenced rat uterine estrogen receptor (GenBank). Several controls were performed to ensure the specificity of the amplified product.

Primer controls: The primers used were from the ligand-binding domain of the estrogen receptor; this domain is unique to this steroid receptor. Moreover, primer sequences spanned intron-exon boundaries to distinguish PCR product obtained from reverse transcribed RNA from that of amplified DNA.

Specificity of product: Rat uterine RNA, reverse transcribed and amplified with the same primer sets (performed concurrently with analyses of PC12 cell RNA), also revealed 300 and 200 base pair products (FIG. 2, lanes 3,4,). The sequence of the 200 base pair uterine product was identical to the published sequence of the appropriate domain within the rat uterine estrogen receptor. No bands were seen in RT-PCR reactions containing yeast RNA (FIG. 2, lane 9), which does not express an estrogen receptor but an estrogen-binding protein [10, 26] which has little sequence homology with the estrogen receptor. Similarly, reactions in which no RNA was present (to control for amplification of contaminants) also had no bands (FIG. 2 lane 2). Hence the RT-PCR analyses, like the in situ hybridization data, indicate that estrogen receptor mRNA is expressed in PC12 cells. It should be noted however that, in its present form, the RT-PCR assay was not designed to confirm the qualitative differences between naive and NGF-treated PC12 cells seen by in situ hybridization to the estrogen receptor probe. The assay was used, basically, to corroborate the presence of estrogen receptor mRNA in PC12 cells, and hence the amount of RNA (1 or 2 μg) used for the analysis was tailored for each group to obtain the most optimal PCR signal.

Estrogen binding by PC12 cells:

A modification [90] of the nuclear exchange assay [64] was used to determine the presence of estrogen binding sites in nuclear pellets of PC12 cells. Both naive, NGF-treated, and NGF/estrogen-treated cells were grown in phenol red-free RPMI 1640 medium and 10% gelding serum, but without fetal bovine serum, and deprived of estrogen for 24 hours. Using 11β-methoxy-[$^3$H]-moxestrol, low, but reliable, compatible specific binding (2~4.5 fmols/mg DNA) was detected in naive PC12 cells (FIG. 3A). Mean specific binding in cells exposed to NGF for 3 weeks, on the other hand, increased 6-fold, as compared to untreated cells. Previous exposure to saturating concentrations of estradiol decreased specific estrogen binding in NGF-treated PC12 cells, suggesting that in this cell type, as has been shown for adult neuronal [14] and peripheral [66, 84, 85] target cells, estrogen down-regulates its own receptor. While the estrogenic compound, DES, was able to compete for moxestrol binding sites, the non-aromatizable androgen, DHT, did not, indicating that binding was specific to the estrogen receptor. While estrogen binding increased 6-fold following 21 days of NGF exposure, a time course analysis (FIG. 3B) indicated that a noticeable elevation in estrogen binding was already apparent by 4 days of NGF treatment. No increase was observed, in contrast, after 1 day of NGF exposure.

Estrogen differentially regulates NGF receptor mRNAs:

The question of whether NGF receptor mRNAs were regulated by estrogen in PC12 cells was examined. Cells were grown for 2 weeks in the presence of NGF and then exposed to $10^{-9}$ M estradiol for 1, 3 or 7 days in the continued presence of the factor. NGF-treated cells were used in these experiments, since our data indicated that untreated cells have very low levels of estrogen binding. There were no readily visible effects of estrogen exposure on the morphological response of the cells to NGF. Total RNA was analyzed by Northern blot analyses, using $^{32}$P-labeled cDNA probes for trkA and $p75^{NGFR}$.

trkA mRNA: A very small effect on trkA mRNA was evident at 3 days of estrogen treatment. However, estrogen treatment for 7 days resulted in a consistent and statistically-significant ($p<0.05$) 2-fold increase in the expression of the trkA transcript (FIG. 4A and B).

$p75^{NGFR}$: In the case of $p75^{NGFR}$ mRNA, in contrast, estrogen elicited a transient decrease in the expression of this transcript. The level of $p75^{NGFR}$ was below basal levels 1 day after estrogen treatment and was approximately 50% of baseline ($p<0.05$), following 3 days of estrogen exposure (FIG. 5A and 5B). By 7 days of estrogen treatment, however, the expression of $p75^{NGFR}$ was indistinguishable from basal levels. As has been reported before [70], NGF treatment resulted in an increase in $p75^{NGFR}$ mRNA in PC12 cells, as compared to untreated controls.

III. Discussion

This invention discloses estrogen sensitivity and the potential for reciprocal regulatory interactions between estrogen and NGF in another paradigmatic target of NGF, PC12 cells was examined. Derived from a rat pheochromocytoma, PC12 cells are an established clonal line that, in the presence of serum, does not depend on NGF for survival [35–37]. However, on exposure to NGF these cells cease proliferating, develop processes and differentiate phenotypically into a sympathetic-like neuron. Using in situ hybridization histochemistry, reverse transcriptase-polymerase chain reaction and ligand-binding assays, it is shown that estrogen receptor mRNA and protein (binding sites) are expressed in PC12 cells. The data indicate further that these are functional estrogen receptors in that estrogen appears to regulate the NGF receptor mRNAs differentially in these cells, by up-regulating trkA mRNA and transiently down-regulating $p75^{NGFR}$ MRNA expression. Moreover, it was found that long term NGF treatment significantly increases specific nuclear estrogen binding. These data demonstrate the existence of reciprocal regulation of the estrogen and neurotrophin receptor systems by their ligands.

The present data indicate that PC12 cells are estrogen targets and demonstrate the potential for reciprocal regulation of estrogen and NGF receptor systems by their respective ligands. Estrogen receptor mRNA and specific, compatible nuclear estrogen binding sites are both present in PC12 cells. In addition, it was found that estrogen differentially regulates expression of the NGF receptor MRNA, by transiently down-regulating $p75^{NGFR}$ mRNA and up-regulating expression of trkA mRNA. These findings advance the hypothesis that estrogen sensitivity may be a general feature of neurotrophin targets. As has been demonstrated previously in female rats [90], another prototypical neurotrophin target, the adult sensory neuron, is also estrogen-responsive, and, in these neurons as well, estrogen appeared to differentially regulate $p75^{NGFR}$ and trkA mRNA in a manner similar to that seen in PC12 cells. It was also found that NGF treatment of PC12 cells significantly up-regulates their level of nuclear estrogen binding. Thus, in addition to the capacity for estrogen to regulate responsiveness to the neurotrophins, these findings establish the potential for neurotrophins to regulate neuronal responsiveness to estrogen.

Although PC12 cells have been shown responsive to other members of the steroid receptor superfamily of transcription factors such as glucocorticoids [37, 54] and retinoic acid [86, 87], estrogen receptors have not been previously reported in this cell line. The data indicates, indirectly and directly, that PC12 cells are estrogen sensitive. In situ hybridization and RT-PCR show that estrogen receptor RNA is present in these cells. Binding assays indicate the presence of specific nuclear estrogen receptor in both naive and NGF-treated PC12 cells. Moreover, the effect of estrogen on NGF receptor MRNA expression in PC12 cells provides evidence that estrogen receptors in these cells are functional. Finally, estrogen binding in NGF-treated cells was reduced on exposure to estrogen. This is consistent with its action in other estrogen targets such as the adult brain [14], uterus [66, 85] and MCF-7 tumor cells [84], further supporting the presence of a classical estrogen receptor in PC12 cells.

The relatively low level of estrogen binding observed in naive PC12 cells is consistent with other reports of estrogen sensitivity in adrenal medullary cells. While high levels of estrogen binding are expressed in the adrenal gland [18, 74], autoradiographic [95] and immunohistochemical [44] analyses suggest that most of the estrogen receptor expression is restricted to the adrenal cortex, with very little, if any, expression in the adrenal medulla. Hence, the low level of estrogen binding seen in naive PC12 cells, which are derived from an adrenal medullary tumor, may represent a phenotype characteristic of this cell type. Exposure of PC12 cells to NGF, on the other hand, increased the level of estrogen binding. The level of estrogen binding in NGF-treated cells is within the range reported for other adult neural targets of estrogen, such as the cerebral cortex [31] and DRG [90]. Moreover, the effect of NGF on estrogen binding in PC12 cells is consistent with the action of another growth factor on estrogen receptors, namely, the epidermal growth factor [7], which has been shown to induce estrogen receptors in the human breast carcinoma cell line, MCF-7.

The NGF-induced increases in estrogen binding in PC12 cells may result from transcriptional, translational or post-translational modifications of the estrogen receptor. At the present time, none of these mechanisms can definitively be excluded. For example, since phosphorylation of the estrogen receptor is believed to increase estrogen binding [28, 29], one possible mechanism of NGF action may result from this post-translational modification. However, the relatively slow time course of the effect of NGF on estrogen binding levels would not appear to favor this possibility. Alternatively, NGF may act by increasing the number of estrogen receptors, by increasing either the rate of translation or transcription of estrogen receptor mRNA. Some support for this hypothesis lies in the in situ hybridization analysis, where hybridization to the estrogen receptor probe was markedly enhanced in NGF-treated cells, as compared to the naive cells. However, in view of the differences in morphology and cytoplasmic content of the naive and NGF-treated cells, as well as the difficulty of RNA quantitation by non-isotopic in situ hybridization, this difference in hybridization to the estrogen receptor probe remains to be validated.

Estrogen and NGF had differential actions on mRNA expression of the pan-neurotrophin receptor, $p75^{NGFR}$ On exposure to estrogen, NGF-treated cells exhibited a transient decrease in $p75^{NGFR}$ mRNA. An estrogen-dependent, transient down-regulation of $p75^{NGFR}$ mRNA was also seen in adult sensory neurons [90], when estrogen was administered to ovariectomized females. Similarly, $p75^{NGFR}$ was also decreased in the septum of adult ovariectomized females replaced with estrogen, as compared to ovariectomized controls [33]. Down-regulation of $p75^{NGFR}$ mRNA may be a common action of the gonadal hormones. In the developing basal forebrain and cerebellum, the markedly lower levels of $p75^{NGFR}$ mRNA reported in males, as compared to females [52], are paralleled by significant pre- and post-natal surges of androgen that occur only in the male. More direct evidence of androgen effects on this gene have been reported in the adult testis, where testosterone was shown to decrease $p75^{NGFR}$ mRNA in Sertoli cells [80]. The NGF-induced increase in $p75^{NGFR}$ MRNA shown earlier [70] was observed in this study as well.

In contrast to its actions on $p75^{NGFR}$ mRNA, estrogen increased the expression of trkA mRNA in PC12 cells. This effect appeared to be delayed in comparison to the effects of estrogen on $p75^{NGFR}$. Although the time points are not strictly comparable, it has been observed that a similar effect of estrogen on trkA mRNA in adult sensory neurons in vivo, where trkA mRNA was increased approximately two-three-fold, 4 h after a single pulse of estrogen and remained up-regulated at 52 h [90]. One explanation for the transient effects of estrogen on $p7^{NGFR}$ mRNA in PC12 cells may lie in the observation that estrogen markedly down-regulates its own receptor at 7 days of estrogen exposure, and that these reduced levels of estrogen receptor are no longer able to transduce estrogen's effects on $p75^{NGFR}$ mRNA. In the case of trkA mRNA, a significant effect of estrogen is present at 7 days, when estrogen receptor levels are relatively low, although this increase may occur sometime between 3 and 7 days of estrogen. At the present time it can only be hypothesized that either estrogen action on trkA mRNA is indirect, occurring via estrogenic stimulation of an intermediary (at a time when estrogen receptor levels are not suppressed) which then further stimulates trkA mRNA, or that estrogen directly affects trkA, and that the high levels of trkA at 7 days are due, perhaps, to slow turnover or degradation of this mRNA. Although relatively few agents have been shown to increase expression of the trk family of neurotrophin receptors mRNAs, among them, significantly, is retinoic acid, another member of the steroid/thyroid hormone family of transcription factors, which reportedly increases trkB mRNA expression in neuroblastoma cells [49].

The demonstrated responsiveness of PC12 cells to estrogen raises a potential point of concern regarding reproducibility of experiments performed in various laboratories. In the experiments all possible sources of endogenous estrogen or estrogenic influences in the medium were eliminated, including phenol red; an intermittent contaminant of which has been shown to have estrogenic properties [6, 8], and fetal bovine serum, whose endogenous levels of estrogen are in the physiological range. Moreover, the horse serum used has always come from geldings, where steroid levels are below sensitivity of the assay. Thus, if there were low levels of estrogen in the media used in other studies, this could certainly influence experimental outcome and interpretation. In fact, it has recently come to our attention that "donor horse sera" from at least one commercial source, unless strictly specified, may be derived from either gelding (steroid-deficient) or mixed (steroid-containing) herds, and therefore contain varying levels of estrogen.

At the present time the biological and functional consequence of differential regulation of $p75^{NGFR}$ and trkA mRNA by estrogen can only be speculated, in part because it is not yet known how the encoded proteins are regulated by the steroid, and because the individual contribution of these two components to the functional NGF receptor are still under investigation. A recent model suggests that the functional NGF receptor may be composed of a trkA molecule and several $p75^{NGFR}$ molecules, and that binding efficiency, neurotrophin specificity and signal transduction may be related to the ratio of expression of these two forms of the receptor [3, 5, 41]. Hence, by differentially regulating the mRNA for $p75^{NGFR}$ and trkA, estrogen may be in a position to alter the ratio of the two NGF receptors, and consequently, cellular responsiveness to the neurotrophin.

Both NGF and estrogen have been shown to influence neurite outgrowth in the nervous system [55, 103], and NGF has pronounced effects on the morphology of PC12 cells [36, 37]. In the experiments, estrogen did not appear to influence visibly the morphology or neurite differentiation of PC12 cells in either the presence or absence of NGF. In naive PC12 cells, the lack of an estrogen effect on neurite growth may be related to the paucity of estrogen receptors in this condition. However, in NGF-treated cells, in which estrogen binding is increased and estrogen regulates $p75^{NGFR}$ and trkA mRNA, the possible reason for an apparent lack of estrogen effect on neurite outgrowth is less clear. In other cell types, estrogen has been shown to influence transcription of several of the cytoskeletally-related proteins regulated by NGF in PC12 cells, including tau microtubule-associated protein [22, 27, 40], and GAP-43 [25, 62]. Thus it may be that at the dosage used NGF alone maximally stimulates neurite outgrowth in the PC12 system, masking any modulating effects of estrogen on neurite outgrowth, or that additional estrogen-regulatable parameters must be examined.

Reciprocal regulation of estrogen and a growth factor receptor system, similar to the one described in this study, has also been demonstrated in the human breast carcinoma cell line, MCF-7. In this prototypical estrogen target, not only does estrogen stimulate EGF and its receptor [20], but, reciprocally, EGF induces estrogen receptors in these cells [7]. Recent work, demonstrating the co-localization of estrogen and neurotrophin receptors in the developing forebrain [72, 105], suggests that the potential for regulatory interactions between estrogen and neurotrophins is present during neural development. Reciprocal regulation of estrogen-neurotrophin receptor systems by their respective ligands demonstrated in the present study suggests one mechanism by which responsiveness to these important classes of growth-promoting factors may be regulated during neural maturation.

First Series of Experiments
REFERENCES:
1. ALDERSON, R. F., HUA, Z.-W. and HERSH, L. B. (1989) Dev. Brain Res. 48:229–241.
2. BARDE, Y. A., EDGAR, D., THOENEN, H. (1980) Proc. Natl. Acad. Sci. USA 77:1199–1203.

3. BATTLEMAN, D. S., GELLER, A. I., CHAO, M. V. (1993) *J. Neurosci.* 13: 941–951.
4. BEATO, M. (1989) Cell 56:335–344.
5. BENEDETTI, M., LEVI, A., CHAO, M. V. (1993) *Proc. Natl. Acad. Sci., USA* 90: 7859–7863.
6. BERTHIOS, Y., KATZENELLENBOGEN, J. A., KATZENELLENBOGEN, B. S. (1986) *Proc. Natl. Acad Sci. USA* 83:2496–2500.
7. BERTHIOS, Y., DONG, X. F., MARTIN, P. M. (1989) *Biochem. Biophys. Res. Commun.* 159:126–131.
8. BINDAL, R. D., KATZENELLENBOGEN, J. A. (1988) *J. Med. Chem.* 31:1978–83.
9. BURSHELL, A., STATHIS, P. A., DO, Y., MILLER, S. C., FELDMAN, D. (1984) *J. Biol. Chem.* 259:3450–3456.
10. CERARONE, C., BOLOGNESI, C., SANTI, L. (1979) *Hoechst. Anal. Biochem.* 102:188–197.
11. CHAO, M. V. (1992) *Neuron* 5:583–593.
12. CHOMCZYNSKI, P., SACCHI, N. (1987) *Annal. Biochem.* 162:156–159.
13. CIDLOWSKI, J. A., MULDOON, T. G. (1978) *Biol. Reprod.* 18: 234–246.
14. CORDON-CARDO, C., TAPLEY, P., JING, S., NAMDURI, V., O'ROURKE, E., LAMBALLE, F., KOVARY, K., KLEIN, R., JONES, K. R., REICHARDT, L. F., BARBACID, M. (1991) *Cell* 66:173–183.
15. CSILLICK, B. (1987) *Acta Phvsiol. Hungarica* 69:355–361.
16. CURRAN, T., MORGAN, J. I. (1985) *Science* 224:1265–1268.
17. CUTLER, J. B., BARNES, K. M., SAUER, M. A., LORIAUX, D. L. (1978) *Endocrinology* 102:252–257.
18. DEKLOET, E. R., VOORHUIS, D. A .M., BOSCHMA, Y., ELANDS, J. (1986) *Neuroendocrinology* 44:415–421.
19. DICKSON, R. B., LIPPMAN, M. E. (1987) *Endo Rev* 8:29–43.
20. DOHANICH, G. P., WITCHER, J. A., WEAVER, D. R., CLEMENS, L. G. (1982) *Brain Res.* 241:347–350.
21. DRUBIN, D. G., FEINSTEIN, S. C., SHOOTER, E. M., KIRSCHNER, M. W. (1985) *J. Cell Biol.* 101:1799–1807.
22. EDGAR, D. H., THOENER, H. (1978) *Brain Res.* 154:186–190.
23. EICHLER, M. E., RICH, K. M. (1989) *Brain Res.* 482:340–346.
24. EVANS, R. M. (1988) *Science* 540:889–895.
25. FEDEROFF, H. J., GRABCZYK, E., FISHMAN, M. C. (1988) *J. Biol. Chem.* 263:19290–19295.
26. FELDMAN, D., DO, Y., BURSHELL, A., STATHIS, P. A., LOOSE, D. S. (1982) *Science* 218:297–298.
27. FERREIRA, A., CACERES, A. (1991) *J. Neurosci.* 11:392–400.
28. FLEMING, H., BLUMENTHAL, R., GURPIDE, E. (1982) *Endocrinology* 111:1671–1677.
29. FLEMING, H., BLUMENTHAL, R., GURPIDE, E. (1983) *Proc. Natl. Acad. Sci. USA* 80:2486–2490.
30. FRANKFURT, M., GOULD, E., WOOLLEY, C., MCEWEN, B. S. (1990) *Neuroendocrinology* 51:530–535.
31. FRIEDMAN, W. J., MCEWEN, B. S., TORAN-ALLERAND, C. D. and GERLACH, J. L. (1983) *Dev. Brain Res.* 11:19–27.
32. FUSCO, M., ODENFELD-NOWAK, B., VANTINI, G., SCHIAVO, N., GRADKOWSKA, M., ZAREMBA, M., LEON, A. (1989) *Neuroscience* 33:47–52.
33. GIBBS, R., PFAFF, D. W. (1992) *Broca. Exp. Neurol.* 116:23–39.
34. GNAHN, H., HEFTI, F., HEUMANN, R., SCHWAB, M., THOENEN, H. (1983) *Dev. Brain. Res.* 9:45–52.
35. GREENE, L. A. (1978) *Adv. Pharmacol. Ther.* 10:197–206.
36. GREENE, L. A., TISCHLER, A. S. (1976) *Proc. Natl. Acad. Sci. USA* 73:2424–2428.
37. GRENNE, L. A., TISCHLER, A. S. (1982) *Adv. Cell. Neurobiol.* 3:373–414.
38. GUO, J. Z., GORSKI, J. (1988) *Mol. Endocrinol.* 2:693–700.
39. HAMMER, R. P., JACOBSON, C. D. (1984) *Int. J. Dev. Neurosci.* 2:77–85.
40. HEMPSTEAD, B. L., MARTIN-ZANCA, D., KAPLAN, D. R., PARADA, L. F., CHAO, M. V. (1991) *Nature* 350:678–683.
41. HANEMAAIJER, R., GINZBURG, I. (1991) *J. Neurosci. Res.* 30:163–171.
42. HENKE, R. C., TOLHURST, O., SENTRY, J. W., GUNNING, P., JEFFREY, P. L. (1991) *Neurochem. Res.* 16:675–679.
43. HIGGINS, G. A., KOH, S., CHEN, K. S., GAGE, F. H. (1989) *Neuron* 3:247–256.
44. HIRST, J. J., WEST, N. B., BRENNER, R. M., NOVT, M. J. (1992) *J. Clin. Endocrinol. Metab.* 75:308–314.
45. IP, N. Y., STITT, T. N., TAPLEY, P., KLEIN, R., GALSS, D. J., FANDL, J., GREENE, L. A., BARBACID, M., YANCOPOULOS, G. D. (1993) *Neuron* 10:137–149.
46. JOHNSON, E. M., GORIN, P. D., BRANDIES, L. D., PEARSON, J. (1980) *Science* 210:916–918.
47. KAISHO, Y., SHINTANI, A., ONO, Y., KATO, K., IGARASHI, K. (1991) *Biochem. Biophys. Res. Comm.* 174:379–385.
48. KAPLAN, D. R., HEMPSTEAD, B. L., MARTIN-ZANCA, D., CHAO, M. V., PARADA, L. F. (1991a) *Science* 252:554–558.
49. KAPLAN, D. R., MARTIN-ZANCA, D., PARADA, L. F. (1991b) *Nature* 350:158–160.
50. KAPLAN, D. R., MATSUMOTO, K., LUCARELLI, E., THEILE, C. J. (1993) *Neuron* 11:321–331.
51. KLEIN-HITPASS, L., SCHORPP, M., WAGNER, U., RYFFEL, G. U. (1986) *Cell* 46:1053–1061.
52. KOIKE, S., SAKAI, M., MARAMATSU, M. (1987) *Nuc. Acids Res.* 15:2499–2513.
53. KORNACK, D. R., LU, B., BLACK, I. B. (1991) *Brain Res.* 542:171–174.
54. LAMBALLE, F., KLEIN, R., BARBACID, M. (1991) *Cell* 66:967–979.
55. LEVI, A., BIOCCA, S., CATTANEO, A., CALISSANO, P. (1988) *Mol. Neurobiol.* 2:201–226.
56. LEVI-MONTALCINI, R. (1987) *EMBO J* 6:1145–1154.
57. LINDSAY, R. M. (1988) *J. Neurosci.* 8:2394–2405.
58. LOOSE-MITCHELL, D. S., CHIAPPETTA, C., STANCEL, G. M. (1988) *Mol Endocrinol* 2:946–951.
59. LUINE, V. N. (1985) *Exp. Neurol.* 89:484–490.
60. LUINE, V. N., KHYLCHEVSKAYA, R. I., MCEWEN, B. S. (1975) *Brain Res.* 86:293–306.
61. LUINE, V. N., REMMER, K. J., MCEWEN, B. S. (1986) *Endocrin.* 115:874–878.
62. LUSTIG, R. H., SUDOL, M., PFAFF, D. W., FEDEROFF, H. J. (1991) *Mol. Brain Res.* 11:125–132.
63. MACLUSKY, N. J., MCEWEN, B. S. (1978) *Nature* 274:276–278.
64. MACLUSKY, N. J., BROWN, T. J., JONES, E., LERANTH, C., HOCHBERG, R. B. (1990) Autoradiographic and microchemical methods for quantitation of steroid receptors. In: *Methods in Neurosciences Vol 3, Quantitative and qualitative microscopy (Conn PM, ed),* pp 1–35. New York: Academic Press.

65. MAISONPIERRE, P. C., BELLUSCIO, L., FRIEDMAN, B., ALDERSON, R. F., WIEGAND, S. J., FURTH, M. E., LINDSAY, R. M., YANCOPOULOS, G. D. (1990a) Neuron 5:501–509.
66. MANNI, A., BAKER, R., ARAFAH, B. M., PEARSON, O. H. (1981) J. Endocrinol. 6:281–287.
67. MARTIN-ZANCA, D., OSKAM, R., MITRA, G., COPELAND, T., BARBACID, M. (1989) Mol. Cell Biol. 9:24–33.
68. MATSUMOTO, A., ARAI, Y. (1981) J. Comp. Neurol. 197:197–206.
69. MATSUMOTO, A., MURAKAMI, S., ARAI, Y. (1988) Cell Tiss. Res. 252:33–37.
70. MILLER, F. D., MATHEW, T. C., TOMA, J. G. (1991) J. Cell Biol. 112:303–312.
71. MIRANDA, R. C., TORAN-ALLERAND, C. D. (1992) Cerebral Cortex 2:1–15.
72. MIRANDA, R. C., SOHRABJI, F., TORAN-ALLERAND, C. D. (1993) Mol. Cell. Neurosci. In press.
73. MUKKU, V., STANCEL, G. M., (1985) J. Biol. Chem. 260:9820–9824.
74. MULLER, R. E., WOTIZ, H. H. (1978) J. Biol. Chem. 253:740–745.
75. NEBREDA, A. R., MARTIN-ZANCA, D., KAPLAN, D. R., PARADA, L. F., SANTOS, E. (1991) Science 252:558–561.
76. NELSON, K. G., TAKAHASHI, T., BOSSERT, N. L., WALMER, D. K., MCLACHLAN, J. A. (1991) Proc Natl Acad Sci USA 88:21–25.
77. NISHIZUKA, N., ARAI, Y. (1981) Brain Res. 212:31–38.
78. NISHIZUKA, N., ARIA, Y. (1982) Proc. Natl. Acad. Sci. USA 79:7024–7026.
79. O'MALLEY, B. (1990) Mol. Endo. 4:363–369.
80. PERSSON, H., AYER-LE LIEVRE, C., SODOR, O., VILLAR, M. J., METSIS, M., OLSON, L., RITZEN, M., HOKFELT, T. (1990) Science 247:704–707.
81. PHILLIPS, H., HAINS, J. M., LARAMEE, G. R., ROSENTHAL, A., WINSLOW, J. W. (1990) Science 250:290–294.
82. RICH, K. M., DISCH, S. P., EICHLER, M. E. (1989) J. Neurocytol. 18:569–576.
83. ROMANO, G. J., HARLAN, R. E., SHIVERS, B. D., HOWELLS, R. D., PFAFF, D. W. (1988) Mol. Endocrinol. 2:1320–1328.
84. SACEDA, M., LIPPMAN, M. E., CHAMBON, P., LINDSAY, R. L., PONGLIKITMONGKIL, M., PUENTE, M., MARTIN, M. B. (1988) Mol. Endocrinol. 2:1157–1162.
85. SARFF, M., GORSKI, J. (1971) Biochem. 10:2557–2563.
86. SCHIEBE, R. J., GINTY, D. D., WAGNER, J. A. (1991) J. Cell Biol. 113:1173–1182.
87. SCHEIBE, R. J., WAGNER, J. A. (1992) J. Biol. Chem. 267:17611–17616.
88. SEHGAL, A., PATIL, N., CHAO, M. V. (1988) Mol. Cell. Biol. 8:3160–3167.
89. SHUPNIK, M. A., ROSENZWEIG, B. A. (1991) J. Biol. Chem. 266:17084–17091.
90. SOHRABJI, F., MIRANDA, R. C., TORAN-ALLERAND, C. D. (1994) J. Neurosci. 14:459–471.
91. SOPPET, D., ESCANDON, E., MARANGOS, J., MIDDLEMAS, D. S., REID, S. W., BLAIR, J., BURTON, L. E., STANTON, B. R., KAPLAN, D. R., HUNTER, T., NIKOLICS, K., PARADA, L. F. (1991) Cell 65:895–903.
92. SQUINTO, S. P., STITT, T. N., ALDRICH, T. H., DAVIS, S., BIANCE, S. M., RADZIEJEWSKI, C., GLASS, D. J., MASIAKOWSKI, P., FURTH, M. E., VALENZUELA, D. M., DDSTEFANO, P. S., YANCOPOULOS, G. D. (1991) Cell 65:885–893.
93. STANLEY, H. F., BORTHWICK, N. M., FINK, G. (1986) Brain Res. 370:215–222.
94. STANLEY, H.F., FINK, G. (1986) Brain Res. 370:223–231.
95. STUMPF, W. H. (1969) Endocrinol. 85:31.
96. THOENEN, H., BARDE, Y. A. (1980) Physiol. Rev. 60:1284–1335.
97. TORAN-ALLERNAD, C. D. (1976) Brain Res. 106:407–412.
98. TORAN-ALLERAND, C. D. (1980) Brain Res. 189:413–427.
99. TORAN-ALLERAND, C. D. (1984) Prog. Brain Res. 61:63–98.
100. TORAN-ALLERAND, C. D., GERLACH, J. L., MCEWEN, B. S. (1980) Brain Res. 184:517–522.
101. TORAN-ALLERAND, C. D., HASHIMOTO, K., GREENOUGH, W. T., SALTARELLI, M. (1983) Dev. Brain Res. 7:97–101.
102. TORAN-ALLERAND, C. D., ELLIS, L., PFENNINGER, K. (1988) Dev. Brain Res. 41:87–100.
103. TORAN-ALLERAND, C. D. (1991) Psychoneuroendocrinology 16:7–24.
104. TORAN-ALLERAND, C. D., MIRANDA, R. C. (1993) Combining non-isotopic in situ hybridization with steroid autoradiography. In: J. Eberwine, J. Barchus and K. Valentino (Eds), In Situ Hybridization in Neurobiology, 2nd Edition, New York, Oxford University Press, (In Press).
105. TORAN-ALLERAND, C. D., MIRANDA, R. C., BENTHAM, W., SOHRABJI, F., BROWN, E. J., HOCHBERB, R. B., MACLUSKY, N. J. (1992a) Proc. Natl. Acad. Sci. USA 89:4668–4672.
106. TORAN-ALLERAND, C. D., MIRANDA, R. C., HOCHBERG, R. B., MACLUSKY, N. J. (1992b) Brain Res. 576:25–41.
107. WATERMAN, M. L., ADLER, S., NELSON, C., GREENE, G. L., EVANS, R. M., ROSENFELD, M. G. (1988) Mol. Endocrinol. 2:14–21.
108. WEISZ, A., CICATIELLO, L., PERSICO, E., SCALONA, M., BRESCIANI, F. (1990) Mol. Endocrinol. 4:1041–1050.
109. WEISZ, A., ROSALES, R. (1990) Nucl. Acids Res. 18:5097–5106.
110. WILCOX, J. N., ROBERTS, J. L. (1985) Endocrinology 117:2392–2396.
111. WU, B. Y., FODOR, E. J., EDWARDS, R. H., RUTTER, W. J. (1989) J Biol. Chem. 264:9000–9003.
112. YU, W. H. A., GIBBS, R. B., AND PFAFF, D. W. (1991) Soc. Neurosci. Abstr. 17:226.
113. MURAD F., KURET, J. A. (1990) Estrogens and Progestins. Goodman and Gilman's, the Pharmacolocrical Basis of Therapeutics, Gilman, A. G., et al., eds., Pergamon Press, pp. 1384–1396.
114. FRIDEN, P. M., et al. (1993) Science 259:373–377.
115. The Merck Manual of Diagnosis and Therapy (1992) Berkow, R, et al., eds., Merck Research Laboratories, pp. 1403–1407.

Second Series of Experiments

Estrogen profoundly affects the organization of the nervous system. Its receptor, a nuclear transcription factor, is widely expressed in the developing forebrain. Earlier work established that forebrain estrogen target neurons coexpress nerve growth factor (NGF) receptors and receptor MRNA.

The present study examined the regulation of forebrain estrogen receptors by NGF, using organotypic cultures of the developing cerebral cortex and basal forebrain. NGF significantly increased nuclear estrogen binding in cortical but not basal forebrain explants. Both cortical and basal forebrain explant cultures express the NGF receptor, TrkA. However, the earlier observation that developing cortical neurons, unlike basal forebrain neurons, widely coexpress mRNAs for NGF and its cognate receptors, suggests that in the present study cortical neuronal responses to exogenous NGF may have been primed by autocrine mechanisms. Alterations in nuclear estrogen binding but not estrogen receptor mRNA levels suggests that NGF may regulate cortical estrogen receptors posttranscriptionally.

Gonadal steroid hormones such as the estrogens have an important role in the organization of the developing central nervous system (Arnold and Gorski, 1984; Breedlove, 1992; Toran-Allerand, 1984). Alterations in the gonadal steroid milieu of the developing brain influence critical aspects of differentiation including neurite extension, synapse formation, myelination, and the expression of neurotransmitter systems (for references, see Miranda and Toran-Allerand, 1992). The effects of estrogen are mediated by an intranuclear receptor, a transcription factor homologous to the type II zinc finger class of DNA binding proteins (O'Malley, 1990).

The developing forebrain is an important site for the expression of the estrogen receptor. Estrogen target regions of the developing forebrain exhibit two different temporal patterns of expression. The cerebral cortex expresses high estrogen receptor levels during a restricted developmental window, corresponding to salient periods in cortical differentiation such as cell migration in the cortical plate, the outgrowth of neuronal processes, and the onset of synapse formation and myelination (Friedman et al., 1983; Gerlach et al., 1983; Miranda and Toran-Allerand et al., 1992; Shughrue et al., 1990; Miranda and Toran-Allerand et al., 1992b). During this period, receptor mRNA and protein expression appear to be increasingly restricted to the more superficial laminae (the more immature neurons) of the neocortical plate as well as the cortical subplate, marginal zone, and to limbic cortical structures. In contrast, regions such as the basal forebrain express development but achieve maximal estrogen receptors during development but achieve maximal estrogen receptor expression only in the adult (Gerlach et al., 1983).

In view of the role of estrogen in neural development, factors that regulate the expression of the estrogen receptor will, in turn, control the estrogen-mediated transcriptional machinery of cells within the developing forebrain. Previous work suggested that nerve growth factor (NGF), a member of the neurotrophin family of growth factors, may be in a position to regulate estrogen receptors. Our early work showed that mRNA and protein for the panneurotrophin receptor (p75) colocalize with estrogen binding sites in the developing forebrain (Toran-Allerand et al., 1992a). More recently, it was demonstrated that mRNA for TrkA, the NGF-specific signal transducing receptor, also colocalizes to presumptive estrogen target neurons of the developing forebrain (Miranda et al., 1993b). Furthermore, in NGF-sensitive PC12 cells, NGF stimulated a sixfold increase in estrogen binding sites (Sohrabji et al., 1994a). Hence, the present study examined the role of NGF in the regulation of estrogen receptors and receptor mRNA in two developing telencephalic NGF targets, the cerebral cortex and basal forebrain. Using organotypic explant cultures obtained from neonatal rats we found that exposure to NGF increased the density of estrogen binding sites in the cortex but not the basal forebrain. Additionally, NGF-dependent increases in estrogen binding were not paralleled by an increase in estrogen receptor mRNA, suggesting that the neurotrophin may exert its actions posttranscriptionally on the steroid hormone receptor.

Material and Methods

Tissue Culture

Figure 6A:
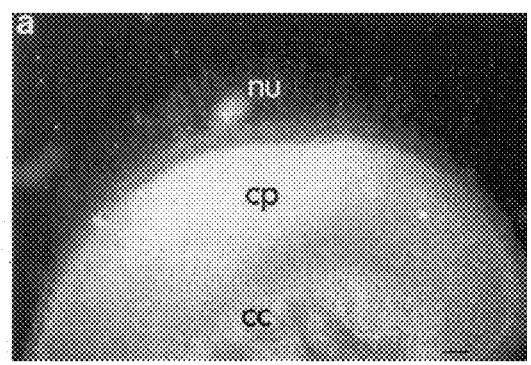
Figure 6B:
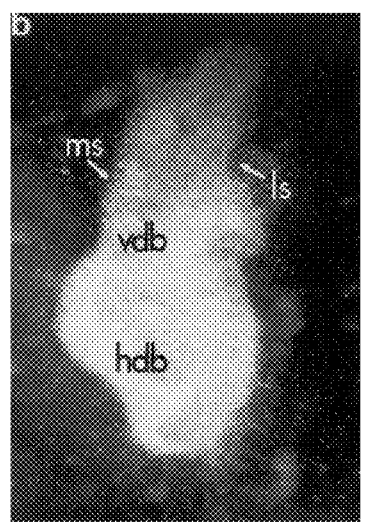
Figure 6C:
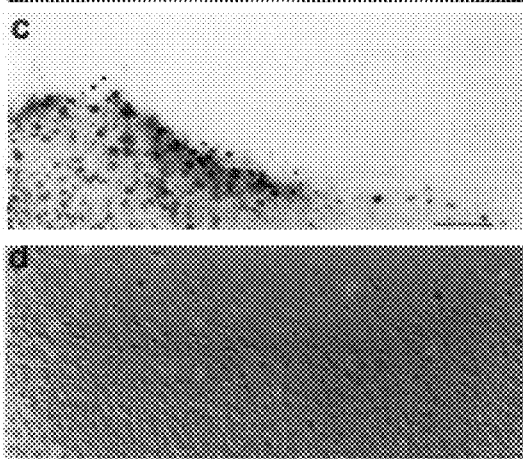

Time-pregnant rats (Sprague-Dawley) were obtained from Zivic (Miller, Pa.). Organotypic explant cultures were obtained from postnatal day (P) 2 rat brains (P1=day of birth) of both sexes. Brains were slice coronally into 360-$\mu$m thick sections using a brain slicer (Toran-Allerand, 1990). A total of four coronal sections from the periseptal region were isolated and dissected into four pairs of hemicoronal cortical [cingulate and neocortex, FIG. 6(a)] and basal forebrain [septum, nuclei of the diagonal band of Broca and ventral pallidum, FIG. 6(b)] sections. Hemicoronal explants were maintained in roller tube assemblies (Caeser et al., 1989; Gahwiler et al., 1991), on collagen coated coverslips for 8 days in vitro, in serum supplemented (25% gelded horse serum, JRH), steroid deficient and phenol red free medium containing 50% basal medium (Eagle's), 25% Hank's balanced salt solution (HBSS), and 0.65% glucose. The result of radioimmunoassays for horse estrogens (equilin, equilinin), estradiol-17$\beta$, total testosterone, DHEA-sulfate, and 17-hydroxyprogesterone indicated that the serum concentrations of each of these gonadal hormones were below the limits of detectability of the assay. Mirror pairs of hemicoronal explants (Toran-Allerand, 1976) were randomly assigned to experimental [human recombinant NGF (hrNGF, gift of Louis Burton, Genetech) treated, 100 ng/mL) and control (non-NGF treated) groups. Cultures were fed 3 times a week.

Immunohistochemistry for Estrogen Receptor

Estrogen receptorlike immunoreactivity was identified in cortical and basal forebrain explant cultures by using polyclonal rabbit antibody (AS409) raised to a rat estrogen receptor-$\beta$-galactosidase fusion protein (gift of Shinju Hayashi, Tokyo Metropolitan Institute for Neurosciences; Hayashi, 1994). Antigen-antibody complexes were detected using a biotinylated secondary antibody and an enzyme (horseradish peroxidase) catalyzed reaction product (ABC Elite kit, Vector), using nickel-diaminobenzidine and hydrogen peroxide as substrates.

Figure 6D:
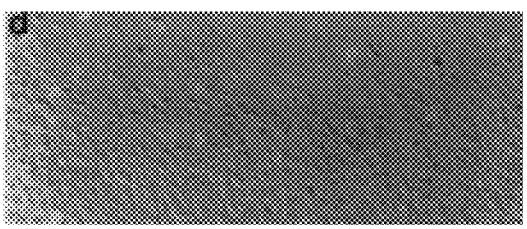

Controls. Incubation with rabbit preimmune serum [FIG. 6(d)] in place of the primary antibody, as well as omission of antibody, resulted in lack of staining in explant cultures.

Western Immunoblot for NGF Receptor, TrkA

Explants (three explants pooled/sample) were homogenized in a buffer containing 50 mM Tris (pH 7.4), 150 mM NaCl, 10% glycerol, 1 mM EGTA, 1 mM Na$_3$VO$_4$ 5 $\mu$M ZNCl$_2$, 100 mM NAF, 10 $\mu$g/mL Aprotinin, 1 $\mu$g/mL Leupeptin, 1 mM phenylmethylsulfonylfluoride (PMSF) and 1% Triton X-100. The homogenate was centrifuged at 100,000×g for 15 min at 4° C. Protein concentrations in the supernatant were determined using the Biorad DC protein assay.

Supernatants (~300 $\mu$g protein) were immunoprecipitated with a pan-Trk Antibody (203, gift of Dr. David Kaplan; Hempstead et al., 1991) for 2 h at 4° C. after which the antibody/Trk immunocomplex was pelleted by the addition of protein A-Sepharose CL-4B (Pharmacia Biotech) in a 10% BSA, 20 mM Tris (pH 7.4) solution. Following multiple washes of the pellet with the homogenization buffer, the protein A Sepharose beads were resuspended in 1× Laemmli buffer and boiled for 5 min prior to electrophoretic separation on a 7.5% polyacrylamide gel. Size-fractionated proteins were transferred onto a supported nitrocellulose membrane (0.22 μm; Biorad Laboratories). The membrane was blocked with 3% BSA (faction V, Sigma) in Tris-buffered saline, containing 0.2% Tween-20, for 3 h and probed with a rabbit polyclonal antibody, raised against the extracellular domain of TrkA (gift of Drs. Douglas Clary and Louis Reichardt; Clary et al., 1994) for 22 h at 4° C. Binding of the anti-TrkA antibody was detected using a secondary antibody (Boehringer Mannheim) conjugated to horseradish peroxidase and visualized on autoradiographic film using enzyme-linked chemiluminescence (ECL, Amersham).

Modified Nuclear Binding Assay for Nuclear Estrogen Binding Sites

Nuclear receptor binding sites were identified using previously published protocols (Sohrabji et al., 1994a,b) and were standardized for this experiment using both MCF-7 cells and hypothalamic tissue. Cortical and basal forebrain cultures were maintained for 8 days in vitro. At the end of this period, cultures were incubated for 2 h at 34° C. with 2 μnM [$^3$H]-moxestol (R2858; specific activity 80 Ci/mmol) in feed (phenol red free RPMI+10% gelded horse serum). The gelded horse serum had undetectable levels of estrogens, androgens, and progesterone (see tissue culture protocol), so that there were no endogenous steroids to compete with the nuclear binding of moxestrol. Control cultures were exposed to [$^3$H]-moxestrol in the presence of an excess (2 mM) of unlabeled diethyl stilbestrol (DES), a synthetic estrogen. The radioligand-containing feed was then removed and the cultures washed and harvested for nuclear pellets by sucrose gradient density centrifugation at 4° C. Radioactivity was eluted from nuclear pellets with 95% ethanol (moxestrol is completely soluble in >50% ethanol) and the radioactivity counted in a liquid scintillation counter. DNA content was assayed fluorometrically using the Hoechst dye 33258. Specific binding was determined as the difference between total binding and non-specific binding (in the presence of an unlabeled competing ligand) and the data expressed as femtomoles of specifically bound [$^3$H]-moxestrol/mg DNA. Binding was normalized to DNA rather than to protein, because protein values would be altered by the presence of substrate (collagen) on which the cultures were grown.

Controls. A 1000-fold molar excess of DES (specific estrogen receptor ligand) but not dihydrotestosterone (a nonaromatizable androgen) or progesterone led to a displacement of $^3$H-moxestrol. The absolute levels of non-specific binding remained constant from experiment to experiment. Scatchard analysis on sectioned hypothalamic tissue and MCF7 cells using this protocol, indicated the presence of a single binding site with a dissociation constant ($K_d$=0.86 nM for P14 hypothalamus, 0.7–0.78 nM for MCF7 cells) and maximal binding ($B_{mas}$=310 fmol/mg DNA for P14 hypothalamus and 1800–2500 fmol/mg DNA for MCF7 cells) within the expected range. The dose of [$^3$H]-moxestrol used was sufficient to saturate binding sites in MCF-7 cultures and rat hypothalamus.

Reverse Transcriptase-Polymerase Chain Reaction (RT-PCR)

Estrogen receptor mRNA expression was assessed by semiquantitative RT-CPR, using RNA isolated from pooled cortical (two explants pooled/sample) and basal forebrain (four explants pooled/sample) cultures. PCR primers (gift of B. Schachter, Mount Sinai Hospital) were designed to amplify a 300 base pair (bp) sequence from the region coding for the ligand binding domain (Sohrabji et al., 1994b). Template cDNA formation was primed by reverse primers for the estrogen receptor (3.3 μM) and cyclophilin (1.25 μM) at 42° C. for 45 min. Following heat denaturation of RT, template cDNA was amplified by the addition of gene specific $^{32}$P-labeled forward primers at a final concentration of 0.66 μM, with thermostable DNA polymerase (2.5U/100 mL; AmpliTaq, Perkin-Elmer Cetus). The PCR program, 94° C. for 30 s, 40° C. for 30 s, 75° C. for 90 , was cycled 35 times (amplification occurred within the linear range for this primer set and transcript). Amplified product was size fractionated on a 5% nondenaturing polyacrylamide gel and the product visualized by film autoradiography. The density of estrogen receptor mRNA expression was normalized to concurrently amplified cyclophilin, mRNA.

Controls

Sequence analysis of the 300 bp-PCR product of the estrogen receptor specific primers confirmed that this product was identical to previously reported sequences (Koike et al., 1987) for the rat estrogen receptor mRNA (Sohrabji et al., 1994a). Amplification was performed within the linear range for the detection of estrogen receptor mRNA. To control for differences in the RNA content of the pooled explant samples, an unrelated transcript (cyclophilin) was also reverse transcribed simultaneously, but amplified by PCR in parallel tubes, because the abundance of cyclophilin template interfered with the detection of the estrogen receptor cDNA. As can be observed in FIG. 9, variations in cyclophilin mRNA content correlated with variations in estrogen receptor mRNA. To preclude artifactual DNA amplification, primers were designed to cross intron-exon boundaries. Hence, no bands were seen in control experiments where samples were amplified without prior reverse transcription.

In Situ Hybridization

Estrogen receptor mRNA was detected in cerebral cortical cultures in using $^3$S-labeled oligonucleotide probes complementary to a sequence within rat estrogen receptor mRNA coding for hormone binding domain (Miranda et al., 1993b, 1994; Miranda and Toran-Allerand, 1992; Toran-Allerand et al., 1992b). Following hybridization, cultures were washed 15° C. below the melting temperature ($T_m$, 60° C). Isotopically ($^{35}$S)-labeled hybrids were detected in whole explant cultures by desiccating the cultures and apposing them to autoradiographic film (Kodak X-omat). The intensity of mRNA expression was quantified as the density of film exposure over the explant divided by the density over background using a standard morphometrics package (Jandel Scientific).

Controls. Controls for probe and method specificity have been extensively documented (Miranda et al., 1993a,b, 1994; Miranda and Toran-Allerand, 1992b; Toran-Allerand et al., 1992b). Sense strand hybridization did not result in a detectable signal. Northern analysis of rat uterine mRNA indicates that the antisense probe hybridizes to mRNA of the expected size (6.7 Kb) size. Thermal stability analysis indicates that the probe hybridizes to one single complementary sequence in target mRNA and that the predicted $T_m$ for the probe is very close to an empirically determined $T_m$.

Statistical Analysis

Data were analyzed using a standard statistical package (SASS 5.0.2). t Tests were used in the case of two group comparisons (in situ analysis). In the case of multiple group comparisons (binding assays, RT-PCR analysis), data was first analyzed by NOVAS followed by limited, hypothesisdriven post-hoc comparisons using the Duncan multiple range test. Data was expressed in terms of mean ±SEM.

Results

Expression of Estrogen Receptor Protein/Binding Sites

Cortical and basal forebrain cultures maintained for 8 days in vitro [FIG. 6(a,b)] under the conditions described in the Materials and Methods section, express both estrogen binding sites and estrogen-receptorlike immunoreactivity. Specific nuclear estrogen binding was observed in both cerebral cortical (41.8±12.3 fmol/mg DNA) and basal forebrain (20.95±7.09 fmol/mg DNA) explant cultures. Immunohistochemical analysis confirmed the presence of estrogen-receptorlike immunoreactivity in whole mounts of explant cultures of the cerebral cortex and basal forebrain. The polyclonal rat-specific estrogen receptor antibody was clearly localized to the nuclei of cortical and basal forebrain neurons, an example of which is shown in FIG. 6(c).

Expression of TrkA Protein in Cortical Explant Cultures.

Western analysis of protein Immunoprecipitates obtained from cortical explant cultures, with the specific polyclonal anti-TrkA antibody, indicated the presence of a band of approximately 140 kDa, corresponding to the molecular weight of TrkA (FIG. 7). This band comigrated with the TrkA signal, obtained by immunoprecipitating 300 μg protein from undifferentiated PC12 cells, a well-established NGF-responsive cell line. No signal corresponding to TrkA was observed in the PC12 cell subclone NNR5 that is known to be TrkA receptor deficient (wildtype and mutant NNR5 PC12 cells were a gift of Lloyd Greene; Loeb and Greene 1993). TrkA signal also could be observed in vivo (data not shown), by Western analysis of postnatal day 2, rat cortex immunoprecipitates, at the age at which cortical cultures were explanted indicating that the expression of TrkA was not related to the culturing of cortical explants. The expression f TrkA in cortical explant cultures (relative to non-NGF-treated, undifferentiated PC12 cells), indicates the presence of a substantial receptor substrate for NGF actions.

NGF-Mediated Increases in Estrogen Receptor Binding

Figure 8:
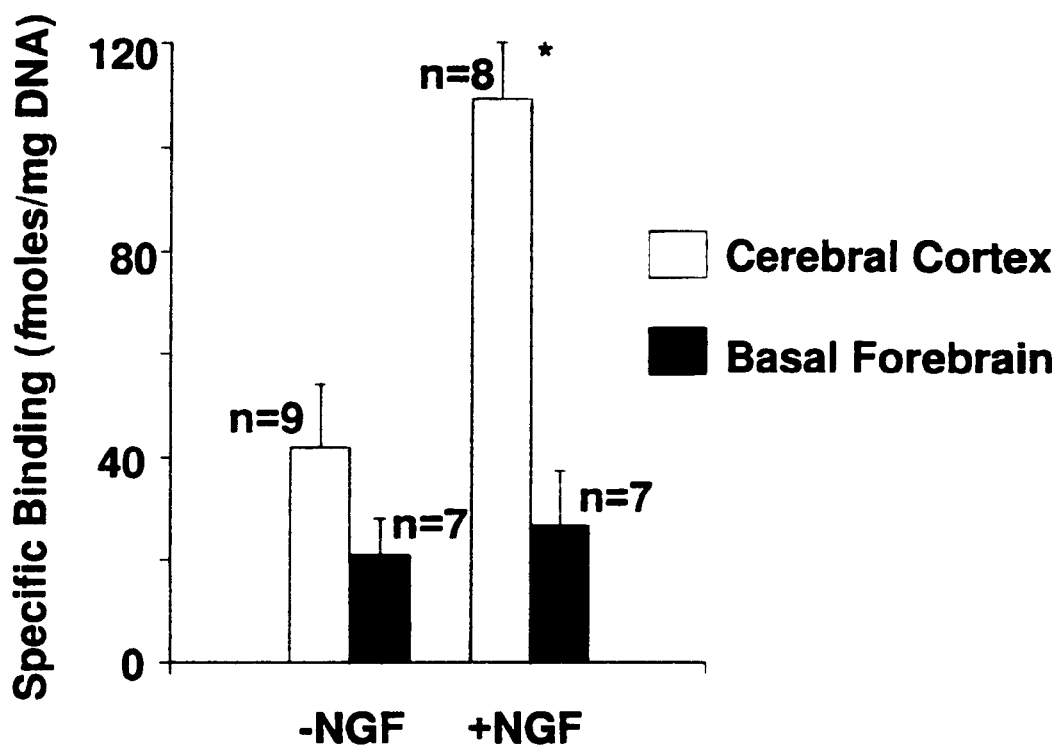

Neurotrophin-mediated changes in estrogen receptor density were assayed by the modified nuclear binding assay, which identifies functional estrogen binding sites. As indicated in FIG. 8, the addition of exogenous human recombinant NGF (hrNGF) let to a 262% increase in nuclear estrogen binding sites (p<0.03) in cortical explant cultures, but did not significantly alter the density of estrogen binding sites in basal forebrain cultures.

NGF-Mediated Changes in Estrogen Receptor mRNA

Figure 9B:
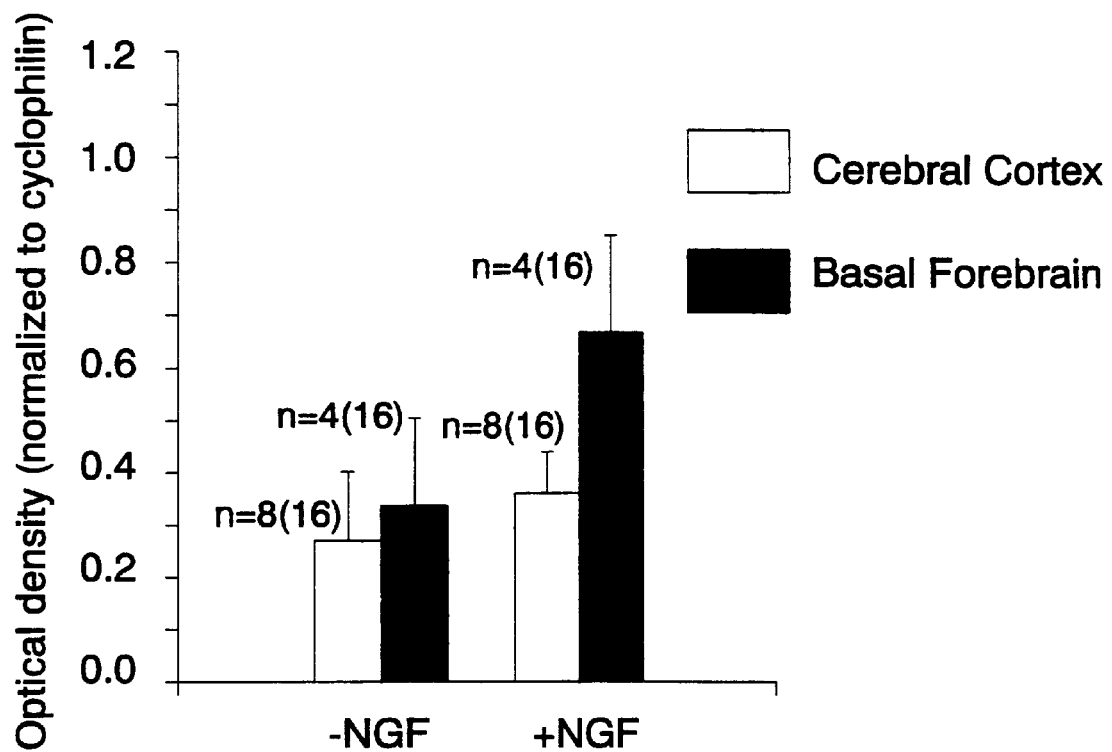

Two assays were used to quantify NGF-dependent changes in estrogen receptor mRNA. Because each explant culture frequently yield less than 1 μg of total RNA, estrogen receptor mRNA expression was assayed by RT-PCR and additionally, in cortical explant cultures, by isotopic in situ hybridization as well. Primers specific to the estrogen receptor were designed to amplify a 300-bp sequence corresponding to a portion of the region coding of the ligand binding domain (Sohrabji et al., 1994a). As seen in FIG. 9, the expression of the 300-bp fragment corresponding to estrogen receptor mRNA, normalized to concurrently reverse transcribed and amplified cyclophilin mRNA (internal control), was no different in the hrNGF-treated group as compared to the control (hrNGF-deprived) group. The amplified 300-bp product was sequenced and found to be identical to the known rat estrogen receptor (Koike et al., 1987: Sohrabji et al., 1994a). Isotopic in situ hybridization, using a 48-bp oligonucleotide probe specific for estrogen receptor mRNA (Miranda et al., 1993b) was used to verify the RT-PCR analyses, as seen in FIG. 10. No alterations in the density of the hybridization signal were observed following the exogenous addition of hrNGF to cortical explant cultures.

Experimental Discussion

Estrogen receptors bind to consensus DNA elements to regulate a host of genes critical to the process of cellular differentiation (Berry et al., 1989; Berthois et al., 1989; Dickson and Lippman, 1987; Dohanich et al., 1982; Ferreira and Caceres, 1991; Gaub et al., 1990; Gou and Gorski, 1988; Kato et al., 1992; Klein-Hitpass et al., 1986; Klungland et al., 1993; Loose-Mitchell et al., 1988; Lustig et al., 1991; Mukku and Stancel, 1985; Perez et al., 1988; Romano et al., 1988; Shughrue and Dorsa, 1994; Sohrabji et al., 1994a,b; Weisz et al. 1990; Weisz and Rosales, 1990) in both neural and nonneural estrogen targets. Hence, identifying factors that regulate the estrogen receptor during periods of cellular differentiation and survival is crucial to our understanding of the mechanisms of estrogen action during neural development. The explant culture paradigm, employed in the present study, provides an important tool for identifying such growth factors and cytokines. Our data indicate that estrogen receptors (identified by binding assay and immunoreactive product) and estrogen receptor mRNA (as determined by in situ hybridization and RT-PCR) are both present in explant cultures of the cerebral cortex and basal forebrain maintained in vitro for a period of 8 days. Furthermore, exposing cultures to hrNGF during this period significantly increases estrogen binding sites in the cerebral cortex but not in the basal forebrain.

Previous work from this laboratory indicated that NGF was a likely candidate for regulating estrogen receptors. For example, the NGF receptors p75 and TrkA, colocalize to estrogen receptor mRNA-expressing neurons in the many regions of the developing forebrain, including the cerebral cortex and basal forebrain, indicating a potential biological substrate for steroid-neurotrophin interactions (Miranda et al., 1993a,b, 1994; Toran-Allerand et al., 1992a). Moreover, in the NGF-sensitive adrenal pheochromocytoma cell line (PC12), estrogen binding was significantly enhanced following a 3-week exposure to NGF (Sohrabji et al., 1994a). Data presented here indicate that cortical explant cultures express functional TrkA, the signal transduction receptor for NGF's actions. Furthermore, the expression of TrkA in cortical explants, albeit less than that of naive (non-NGF treated) undifferentiated PC12 cells, suggests that the developing cerebral cortex is also a likely target of NGF.

The data indicate that NGF leads to a significant upregulation of estrogen binding site density in the cerebral cortex. Substantial data have convincingly demonstrated that nuclear estrogen binding sites are transiently upregulated in vivo in the developing cerebral cortex (Friedman et al., 1983; Gerlach et al., 1983; Miranda and Toran-Allerand et al, 1992; Shughrue et al., 1990; Toran-Allerand et al., 1992b). The mechanisms underlying the transient upregulation of cortical estrogen receptors are as yet unclear. However, comparison of our data with previous reports from other laboratories (Friedman et al., 1983) suggests that the addition of exogenous hrNGF alone leads to an upregulation of specific cortical estrogen binding sites that is equal to the maximal binding observed in vivo in the developing rodent cerebral cortex. Thus, while multiple regulatory factors many be ultimately identified, our data suggest that the local actions of NFG in the developing cerebral cortex may be one important factor that regulates estrogen receptor expression.

While NGF treatment enhanced estrogen binding in the cortex, it did not affect estrogen receptors in basal forebrain neurons. This result was somewhat surprising, because the basal forebrain is a target of both estrogen and NGF (Miranda et al., 1993b Toran-Allerand et al., 1992a). There are several possible reasons for this differential regulation. NGF-dependent upregulation of estrogen binding in cortical explants after 8 days in vitro, occurs during a stage that corresponds to maximal cortical estrogen receptor expression in vivo (Friedman et al., 1983; Gerlach et al., 1983; Miranda and Toran-Allerand, 1992; Shughrue et al., 1990; Toran-Allerand, 1992b). In contrast, estrogen receptor levels in the basal forebrain have yet to reach maximal (adult) levels. The cerebral cortex is therefore primarily a developmental target of estrogen in contrast to the basal forebrain that is more of an adult target of estrogen. It may be, therefore, that the mechanism regulating estrogen receptor levels in the developing cerebral cortex are very different from the mechanisms regulating estrogen receptors in the developing basal forebrain. It is also possible that regional variation in the ability of NGF to regulate estrogen binding may be related to the explant situation itself. The in vi tro environment at P2 (age of explanation) may not be the same for cerebral cortical explants and those of the basal forebrain. Basal forebrain cultures are more deafferented than the cortical plate, for example, because septal-hippocampal connections are initiated during the late gestational period while corticocortical and descending cortical connections are yet immature (Jakab and Leranth, 1995; Uylings et al., 1990). Thus, basal forebrain cultures may be more axotomized and deafferented than cortical explant cultures, perhaps leading to regional differences in the ability of NGF to regulate estrogen receptors.

Regionally specific regulation of NGF-dependent estrogen binding may also be related to the presence of NGF-mediated autocrine or local paracrine loops present in the developing cerebral cortex, but absent in the developing basal forebrain (Miranda et al., 1993a). The presence of potential autocrine/local paracrine loops, indicated by the coexpression of mRNA for both NGF ligand and receptor, suggests that neurons in the developing cortex may be already primed to response to hrNGF. The exogenous hrNGF, acting perhaps in concert with the priming effect of endogenous NGF (which is lacking in the deafferented culture of the developing basal forebrain), may provide in the cortical neurons the trophic stimulus necessary for increasing estrogen binding sites. Moreover, it was observed that virtually every basal forebrain neuron that express TrkA mRNA also coexpressed p75 mRNA in the P9 rat brain. In contrast, there was little overlap in TrkA and p75 mRNA expression (unpublished observations) in the developing cerebral cortex. The signaling pathway mediated by TrkA in neurons of the cerebral cortex, at the peak of estrogen responsiveness, may therefore be p75 independent. Because affinity, ligand specificity and signal transduction appear to be related to cellular ratios of p75 to TrkA (Battleman et al., 1993; Benedetti et al., 1939; Hempstead et al., 1991), this nonoverlap in expression might perhaps contribute to the regionally specific NGF regulation of the estrogen receptor.

The present data suggest that hrNGF differentially regulates levels of nuclear estrogen binding sites and estrogen receptor mRNA. While hrNGF upregulated nuclear estrogen binding sites in cerebral cortical explant cultures, estrogen receptor mRNA was not altered. Although these data do not completely eliminate transcriptional regulation (i.e., a simultaneous increase in transcription coupled to an opposing and equal decrease in message stability), they suggest a possibility that NGF may posttranscriptionally or posttranslationally regulate the estrogen receptor. Some evidence suggest that the phosphorylation of the estrogen receptor on both serine and tyrosine residues may be important for hormone (ligand) binding activity (Landers and Spelberg, 1992), Indeed the cortical NGF-mediated increase in binding may reflect altered receptor phosphrylation, and consequently change the affinity of the estrogen receptor (apparent $K_d$) rather than the absolute receptor number (because the dose of moxestrol used, although saturating for MCF-7 cells and hypothalamus, was only 2.3- to 2.9-fold greater than the apparent $K_d$ for the two estrogen targets, respectively). Other growth factors such as insulinlike growth factor 1 are known to regulate the phosphorylation of the estrogen receptor (Aronica and Katzenellenbogen, 1993). NGF acting via the TrkA receptor was previously shown to regulate intracellular signaling pathways and transcription factors via phosphorylation mechanisms (Ginty et al., 1994; Taylor et al., 1994), and thus, may well regulate binding of estrogen to its receptor by similar signal transduction mechanisms.

The data presented here address three important issues. First, the expression of TrkA as observed by Western analysis, strengthens our previous observations that TrkA mRNA is expressed in the developing cerebral cortex (Miranda et al., 1993a, b). Second, our data ties the expression of TrkA mRNA and protein to a biological effect, that is, the regulation of a nuclear transcription factor, the estrogen receptor. This suggests that the expression of TrkA mRNA and protein in the developing cerebral cortex may be biologically relevant. Moreover, this response to NGF appears to specific to the differentiating cerebral cortex. The final important issue is the regulation of the cortical estrogen receptor itself. While the developmental regulation of cortical estrogen receptors and receptor mRNA has been well-established (Friedman et al., 1983; Gerlach et al., 1983; Miranda and Toran-Allerand, 1992; Sughrue et al., 1990; Toran-Allerand et al., 1992b), mechanisms underlying this transient expression have not been elucidated. This repot identifies NGF as one element in the regulation of the cortical estrogen receptor during the period of cortical differentiation.

Second Series of Experiments

REFERENCES

1. ARNOLD, A and GORSKI, R (1984). Gonadal steroid induction of structural difference in the central nervous system. *Annu. Rev. Neurosci.* 7:413–442
2. ARONICA, S. M. and KATZENELLENBOGEN, B. S (1993). Stimulation of estrogen receeptor-mediated transcription and alteration in the phosphorylation state of the rat uterine estrogen receptor by estrogen, cyclic adenosine monophosphate, and insulin-like growth factor. *Mol. Endocrinol.* 7:743–752.
3. BATTLEMAN, D. S., GELLEER, A. I., and CHAO, M. V. (1993). HSV-1 vector mediated gene transfer of the human growth factor receptor p75hNGFR defines high affinity binding. *J. Neurosci* 13:941–951.
4. BENEDETTI, M. LEVI, A., and CHAO, M. (1993). Differential expression of nerve growth factor receptors leads to altered binding affinity and neorotrophin responsivness. *Proc. Natl. Acad. Sci* 90:7859–7863.
5. BERRY, M., NUNEZ, A. M., and CHAMBON, P. (1989). Estrogen-responsive e;ement of the human pS2 gene is an imperfectly palindromic sequence. *Proc. Natl. Acad. Sci. USA* 86:1218–1222.
6. BERTHOIS, Y., DONG, X. F., and MATRIN, P. M. (1989). Regulation of epidermal growth factor by estrogen and antiestrogen in the human breast cancer cell line MCF-7. *Biochem. Biophys. Res. Commun.* 159:126–131.
7. BREEDLOVE, S. M. (1992). Sexual dimorphism in the vertebrate nervous system. *J. Neurosci.* 12:4133–4142
8. CAESER, M. BONHOEFFER, T., and BOLZ, J. (1989). Cellular organization and developement of slice cultures from rat visual cortex. *Exp. Brain Res.* 77:234–244.
9. CLARY, D. , WESKAMP, G., AUSTIN, L., and REICHARDT, L. (1994) TrkA cross-linking mimics neuronal responses to nerve growth factor. *Mol. Biol. Cell* 5:549–563.
10. DICKSON, R. B. and LIPPMAN, M. E. (1987). Estrogenic regulation of growth factor secretion in human breast carcinomas. *Endocr. Rev 8:29–43.*
11. DOHANICH, G. P., WITCHER, J. A., WEAVER. D. R., and CLEMENS, L. G. (1982). Alterations of muscarinic binding in specific brain regions following estrogen treatment. *Brain Res.* 241:347–350.
12. FERREIRA, A., and CACERES, A. (1991). Estrogen enhanced neuite growth: evidence for a selective induction of tau and stable microtubules. *J. Neurosci.* 11:392–400.
13. FRIEDMAN, W. J., MCEWEN, B. S., TORAN-ALLERAND, C. D., and GERLACH, J. L. (1983). Perinatal development of hypothalamic and cortical estrogen deceptors in mouse brain: methodological aspects. *Dev. Brain Res.* 11:19–27
14. GAHWILER, B. H., THOMPSON, S., AUDINAT, E., and ROBERTSON, R. (1991). Organotypic slice cultures od neural tissue. In: *Culturing Nerve Cells.* G. Banker and K. Goslin, Eds. MIT Press, London, pp. 379–411.
15. GAUB, M., BELLARD, M. SCHEUER, L, CHAMBON, P., and SASSONE-CORSI, P. (1990). Activation of the ovalbumin gene by the estrogen receptor involves the fos-jun complex. *Cell* 63:1267–1276.
16. GERLACH, K. L., MCEWEN, B. S., TORAN-ALLERAND, C. D., and FREDMAN, W. J. (1983). Perinatal development of estrogen receptors in mouse brain asserted by radiautography, nuclear isolation and receptor assay. *Dev. Brain Res.* 11:7–18.
17. GINTY, D. D., BONNI, A., and GREENBERG, M. E. (1994). Nerve growth factor activates a rasdependent protein kinase that stimulates c-fos transcription via phosphorylation of CREB. *Cell* 77:713–725.
18. GUO, J. Z. and GORSKI, J. (1988). Estrogen effects on histone messenger RNA levels in rat uterus. *Mol. Endocrinol.* 2:693–700.
19. HAYASHI, S. (1994). Immunocytochemical detection of estrogen receptor in the facial nucleus of the newborn rat by three antibodies with distinct epitopes. *Horm, Behav.* 28:530–536.
20. HEMPSTEAD, B. L., MARTIN-ZANCA, D., KAPLAN, D. R., Parada, L. F., and CHAO, M. V. (1991). High affinity of NGF binding requires the co-expression of the trk proto-incogene and the low affinity receptor. *Nature* 350:678–683.
21. JAKAB, R., and LERANTH, C. (1995). Septum. In: *The Rat Nervous System.* G. Pazinos, Ed. Academic Press, Australia, pp. 405–442.
22. KATO, S., YAMAUCHI, J., MAUSHIOE, S., and CHAMSON, P. (1992). A far upstream estrogen response elemnet of the ovalbumin gene contains several half-palindromic 5'-TGACC-3' motifs acting syncrigistically. *Cell* 68:731–742.
23. KLEIN-HITPASS, L, SCHORPP, M., WAGNER, U., and RYFFEL, G. (1986). An estrogen-responsive element derived from the 5' flanking region of Xenopus vitellogenein A2 gene functions in transfected human cells. *Cell* 46:1053–1061.
24. KLUNOLAND, H., ANDERSON, O., KISEN, G., ALESTROM, P., and TORA, L. (1993). Estrogen receptor binds to the salmon GnRH gene in a region with long palindromic sequences. *Mol Cell. Endoctrinol.* 95:147–154.
25. KOIKE, S., SAKAI, M., and MURAMATSU, M. (1987). Molecular cloning and characterization of rat estrogen receptor cDNA. *Nucleic Acids Res.* 15:2499–2513.
26. LANDERS, J. P. and SPELBERG, T. C. (1992). New concepts in steroid hormone action: transcription factors proto-oncogenes, and the cascade model for steroid regulation of gene expression. *Crit. Rev. Eukaryot. Gene Expr.* 2:19–63.
27. LOEB, D. and GREENE, L. (1993). Transfection with trk restores "slow" NGF binding, effeicent NGF uptake and multiple NCF responses to NGF-nonresponsive PC:2 cells. *J. Neurosci.* 13:2919–2929.
28. LOOSE-MITCHELL, D. S., ChIAPETTA, C., and STANCEL, G. M. (1988). Estrogen regulation of c-fos messenger ribonucleic acid. *Mol. Endocrinol.* 2:946–951.
29. LUSTIG, R. H., STUDOL, M., PFAFF, D. W., amd FEDEROFF, H. J. (1991). Estrogenic regulation and sex demorphism of growth-associated protein 43 kDa (GAP-43) mRNA in the rat. *Mol Brain Res.* 1:125–132.
30. MIRANDA, R., SOHRABJI F., and TORAN-ALLERAND, C. D. (1993a), Neuronal co-localization of mRNAs for neurotrophins and their receptors in the developing central nervous system suggests a potential for autocrine interactions. *Proc Natl. Acad. Sci. USA* 90:6439–6443.
31. MIRANDA, R., SOHRABJI, F., and TORAN-ALLERAND, C. D. (1993b). Presumptive estrogen target neurons express mRNAs for both the neurothrophins and neurotrophin receptors: a basis for potential developemental interactions of estrogen with the neurotrophins. *Mol. Cell. Neurosci.* 4:510–525.
32. MIRANDA, R., SOHRABJI, F., and TORAN-ALLERAND, C. D. (1994). Interactions of estrogen with the neurothrophins and their receptors during neural development. *Holm. Behav.* 28:367–375.
33. MIRANDA, R. and TORAN-ALLERAND, C. D. (1992) Develpomental regulation of estrogen receptor mRNA in the rat cerebral cortex: a non-isotopic in situ hybridization study. *Cereb. Cortex* 2:1–15.
34. MUKKU, V. and STANGEL, G. M. (1985). Estrogen regulates epidermal growth factor receptor. *J. Biol. Chem.* 263:8710–9824.
35. O'MALLEY, B. (1990). The steroid receptor. *Mol. Endocrinal.* 4:363–369.
36. PEREZ, J., ZUCCHI, I., and MAGGI, A. (1988). Estrogenmodulation of the g-aminobutyric acid receptor complex in the central nervous system of the rat. *J. Pharmacol. Exp. Ther.* 244:100–51011.
37. ROMANO, G. J., HARLAN, R. E., SHIVERS, B. D., HOWELLS, R. D., and PFAFF, D. W. (1988). Estrogen increases proenkephalin messenger ribonucleic acid levels in the ventrogmedial hypothalamus of the rat. *Mol. Endocrinol.* 2:1320–1328.
38. SHUGHRUE, P. and DORSA, D. (1994). Estrogen and androgen differentially modulate the growth-associated protein Gap-43 (neuromodulin) messenger ribonucleic acid in postnatal rat brain. *Endocrinology* 134:1321–1328.
39. SOHRABJI, F., GREENE, L., MIRANDA, R. TORANALLERAND, C. D. (1994a). Reciprocal regulation of estrogen and NGF receptors by their ligands in PC12 cells. *J. Neurobiol.* 25:974–988.
40. SOHRABJI, F., MIRANDA, R., and TORAN-ALLERAND, C. D. (1994a). Estrogen differentially regulates estrogen and nerve growth factor receptor mRNAs in adult sensory neurons. *J. Neurobiol.* 14:459–471.
41. SHUGHRUE, P., STUMPF, W. E., MACLUSKY, N. J., ZIELINSKY, J. E., and HOCHBERG, R. B. (1990). Developmental changes in estrogen receptors in mouse cerebral cortex between birth and post weaning studied by autoradiography with 11b methoxy, 16a[125] iodcestradiol, *Endocrinol.* 126:1112–1124.
42. TAYLOR, L. K., SWANSON, K. D., KERIGAN, J., MOBLEY, W., and LANDRETH, G. E. (1994). Isolation and characterization of a nerve growth factorregulated fos kinase from PC12 cells. *J. Biol. Chem.* 269:308–318.
43. TORAN-ALLERAND, C. D. (1976). Sex steriods and the development of the newborn mouse hypothalamus and preoptic area in vitro: implications for sexual differentiation. *Brain Res.* 106:407–412.
44. TORAN-ALLERAND, C. D. (1984). On the genesis of sexual differentiation of the central nervous system, morphogenetic consequences of steroidal exposure and possible role of a-fetoprotein. *Prog. Brain Res.* 61:63–98.
45. TORAN-ALLERAND, C. D. (1990). The brain slicer: anatomical precision for organotypic explant culture. *Brain Res. Bull.* 24:565–568.
46. TORAN-ALLERAND, C. D., MIRANDA, R., BENTHAM, W., SOHRABJI, F., BROWN, T. J. HOCHBERG, R. B., and MACLUSKY, N. J. (1992a). Estrogen receptors colocalize with low-affinity nerve growth factor receptors in cholinergic neurons of the basal forebrain. *Proc. Natl. Acad. Sci. USA* 89:4668–4672.
47. TORAN-ALLERAND, C. D., MIRANDA, R., HOCHBERG, R. B., and MACLUSKY, N. J. (1992b). Cellular variations in estrogen receptor mRNA translation in the developing brain: evidence from combined 1251-estrogen autoradiography and non-isotopic in situ hybridization histochemistry. *Brain Res.* 576:25–41.
48. UYLINGS, H. B. M., VANEDEN, C. G., PARNAVELAS, J. G., and KALSBECK, A. (1990). The prenatal and postnatal development of the rat cortex, In: *The Cerebral Cortex of the Rat.* B. Kolb and R. C. Tees, Eds, MIT Press, Cambridge, Mass., pp. 35–76.
49. WEISZ, A., CICATIELLO, L., PERSICO, E., SCALONA, M., and BRESCIANI, F. (1990). Estrogen stimulates transcription of the c-jun protooncogene. *Mol. Endocrinol.* 4:1041–1050.
50. WEISZ, A. and ROSALES, R. (1990). Identification of an estrogen reponse element upstream of the human c-fos gene that binds the estrogen receptor and the AP-1 transcription factor. *Nucleic Acids Res.* 18:5097–5106.

Third Series of Experiments

Activation of MAP Kinases (ERKs) by Estradiol in Cerebral Cortical Explants: Cross-Coupling of the Estrogen and Neurotrophin Signaling Pathways.

Estrogen and the neurotrophins have important roles in the developing and adult central nervous system (CNS). Previous studies have demonstrated estrogen and neurotrophin receptor co-localization throughout the developing forebrain, suggesting a potential substrate for steroid/neurotrophin interactions. The hypothesis that estrogen/neurotrophin receptor co-expression leads to reciprocal regulation at the level of signal transduction, through cross-coupling of converging estrogen and neurotrophin signaling pathways whose end-points in the nucleus may be the very same genes was tested. Postnatal day 2 cerebral cortex was maintained as organotypic explants in roller tube culture for 7 days. Following 24 hrs of estrogen and neurotrophin deprivation, estradiol's activation of ERKs 1 and 2 (Extracellular-signal Regulated Kinase) was investigated and rapid (by 5 min.) tyrosine phosphorylation of the ERKs (maximal at 30 min.) that persisted for at least 4 hrs. was found. Although estrogen-induced phosphorylation implies activation (required for ERK nuclear translocation) in-gel kinase assays confirmed that phosphorylated ERKs were much more active in phosphorylating MBP as a substrate than untreated controls. In starting to define the pathways leading to ERK activation, it was found that both estradiol and the neurotrphins (NGF, BDNF and NT-4/5, but not NT-3) induced tyrosine phosphorylation of the estrogen receptor. Conversely, and in keeping with the idea of reciprocal cross-coupling of the signal transduction pathways, it was found that estradiol also induced tyrosine phosphorylation of the trk receptors. These results provide a novel and alternative developmental mechanism for estrogen action that would explain how estrogen and the neurotrophins could each regulate the same broad array of ERE (estrogen response element- and non-ERE-containing genes.

Fourth Series of Experiments

PC12-$E_2$ Cells: A Novel Model System for the Study of Estrogen and Neurotrophin Interactions.

It has been previously reported that wild-type, differentiated PC12 pheochromocytoma cells express very low levels of estrogen receptors. Here it is reported that a PC12 cell variant, PC12-$E_2$ (Wu, Bradshaw, J. Cell Physiol. 164:1995), is estrogen responsive and expresses high estrogen receptor level ($\approx$50% of the levels observed in estrogen receptor over-expressing MCF-7 cells). Moreover, although tyrosine phosphorylation of the estrogen receptor appeared to be expressed constitutively, these cells responded to added estrogen. PC12-$E_2$ responsiveness to estrogen was determined morphologically and by measuring estradiol-induced ERK activation. Estradiol phosphorylated ERKs 1 and 2 on tyrosine within 15 min. In constrast, no estradiol-induced ERK stimulation was observed in wild-type, differentiated PC12 cells, suggesting that the estrogen receptor was integral to the response. Morphological studies revealed extensive and rapid NGF induction of neurite outgrowth (within 24 hrs). While estradiol alone appeared to have little effect on neurite growth, the concurrent addition of estradiol and NGF elicited both a synergistic enhancement of neurite growth and apparent mitogenic activity. These cells were utilized to investigate the pathway(s) by which estradiol activates the ERKs. Preliminary co-precipitation experiments show an association between src and estrogen receptor, src with MEK (MAP Kinase/ERK-activating Kinase), and MEK with B-raf, MEK, which phosphorylates the ERKs on tyrosine residues, is known to exist as a complex consisting of at least hsp90 and B-raf. Since both the unliganded estrogen receptor and src are also known to be associated with hsp90, these findings imply a direct association between the estrogen receptor and at least one component of the MAP Kinase cascade (MEK), suggesting a route by which estrogen could activate the ERKs directly.

What is claimed is:

1. A method of increasing the level of estrogen receptors in a sample of neural tissue from a subject which comprises contacting the sample with: (a) estrogen in an amount effective to increase the level of neurotrophin receptors and (b) a neurotrophin in an amount effective to increase the level of estrogen receptors, so as to thereby increase the level of estrogen receptors in the neural tissue.

2. The method of claim 1, wherein the neurotrophin receptors are selected from a group consisting of trkA receptors, trkB receptors, and trkC receptors.

3. The method of claim 1, wherein the neurotrophin is a nerve growth factor.

4. The method of claim 3, wherein the neurotrophin is selected from a group consisting of human recombinant nerve growth factor (NGF), brain-derived neurotrophic factor (BDNF), neurotrophin-3 (NT-3), and neurotrophin-4/5 (NT-4/5).

5. The method of claim 1, wherein the neurotrophin and estrogen are administered concurrently.

6. The method of claim 1, wherein the neurotrophin and estrogen are administered separately.

7. A method of increasing the level of estrogen receptors in neural tissue of a subject which comprises administering to the subject: (a) estrogen in an amount effective to increase the level of neurotrophin receptors and (b) a neurotrophin in an amount effective to increase the level of estrogen receptors, so as to thereby increase the level of estrogen receptors.

8. The method of claim 7, wherein the neurotrophin receptors are selected from a group consisting of trkA receptors, trkB receptors, and trkC receptors.

9. The method of claim 7, wherein the neurotrophin is a nerve growth factor.

10. The method of claim 7, wherein the neurotrophin is selected from a group consisting of human recombinant nerve growth factor (NGF), brain-derived neurotrophic factor (BDNF), neurotrophin-3 (NT-3), and neurotrophin-4/5 (NT-4/5).

11. The method of claim 7, wherein the neurotrophin and estrogen are administered concurrently.

12. The method of claim 7, wherein the neurotrophin and estrogen are administered separately.

13. The method of claim 7, wherein the effective amount of (a) estrogen and (b) neurotrophin induces tyrosine phosphorylation of the estrogen receptors and the effective amount of (a) estrogen induces tyrosine phosphorylation of the neurotrophin receptors.

\* \* \* \* \*